US008389487B2

(12) United States Patent
Bohn et al.

(10) Patent No.: US 8,389,487 B2
(45) Date of Patent: Mar. 5, 2013

(54) SIRNA-MEDIATED GENE SILENCING OF SYNUCLEIN

(75) Inventors: Martha C. Bohn, Chicago, IL (US); Mohan K. Sapru, Naperville, IL (US)

(73) Assignee: Ann & Robert Lurie Children's Hospital of Chicago, Chicago, IL (US)

( * ) Notice: Subject to any disclaimer, the term of this patent is extended or adjusted under 35 U.S.C. 154(b) by 368 days.

(21) Appl. No.: 12/693,101

(22) Filed: Jan. 25, 2010

(65) Prior Publication Data

US 2010/0286242 A1 Nov. 11, 2010

Related U.S. Application Data

(60) Division of application No. 11/726,211, filed on Mar. 21, 2007, now abandoned, which is a continuation-in-part of application No. PCT/US2005/034516, filed on Sep. 27, 2005.

(60) Provisional application No. 60/614,112, filed on Sep. 29, 2004.

(51) Int. Cl.
A01N 43/04 (2006.01)
A61K 31/70 (2006.01)
(52) U.S. Cl. ........ 514/44 A; 514/44 R; 514/55; 435/455
(58) Field of Classification Search ................. None
See application file for complete search history.

(56) References Cited

U.S. PATENT DOCUMENTS

| | | | |
|---|---|---|---|
| 6,573,099 | B2 | 6/2003 | Graham |
| 7,241,618 | B2 | 7/2007 | Agami et al. |
| 7,605,249 | B2 | 10/2009 | Kaemmerer |
| 2002/0037281 | A1 | 3/2002 | Davidson et al. |
| 2004/0023390 | A1 | 2/2004 | Davidson et al. |
| 2004/0096843 | A1 | 5/2004 | Rossi et al. |
| 2004/0180439 | A1 | 9/2004 | Graham et al. |
| 2004/0219671 | A1 | 11/2004 | McSwiggen et al. |
| 2004/0266005 | A1 | 12/2004 | Graham et al. |
| 2007/0031844 | A1 | 2/2007 | Khvorova et al. |

FOREIGN PATENT DOCUMENTS

WO WO 2004/047872 A2 6/2004
WO WO 2005/004794 A2 1/2005

OTHER PUBLICATIONS

Khodr, et al. (2011) An Alpha-Synuclein AAV Gene Silencing Vector Ameliorates a Behavioral Deficit in a Rat Model of Parkinson's Disese, but Displays Toxicity in Dopamine Neurons, Brain Research, v.1395:94-107.*
Abeliovich, Asa et al.; "Mice Lacking α-Synuclein Display Functional Deficits in the Nigrostriatal Dopamine System;" Neuron, vol. 25, 239-252, Jan. 2000.
Arima, Kunimasa et al.; "NACP/α-synuclein immunoreactivity in fibrillary components of neuronal and oligodendroglial cytoplasmic inclusions in the pontine nuclei in multiple system atrophy;" Acta Neuropathol (1998) 96: 439-444.
Bass, B.L.; "The Short Answer"; Nature, v. 411: 428-9.
Bennet, Catherine; "The role of α-synuclein in neurodegenerative diseases;" Pharmacology & Therapeutics 105 (2005) 311-331.
Betarbet, Ranjita et al.; "Chronic systemic pesticide exposure reproduces features of Parkinson's disease;" nature neuroscience; vol. 3, No. 12; Dec. 2000.
Björklund, A. et al.; "Towards a neuroprotective gene therapy for Parkinson's disease: use of adenovirus, AAV and lentivirus vectors for gene transfer of GDNF to the nigrostriatal system in the rat Parkinson model;" Brain Research 886 (2000) 82-98.
Blouin, Véronique et al.; "Improving rAAV production and purification: towards the definition of a scaleable process;" The Journal of Gene Medicine; *J Gene Med* 2004; 6: S223-S228.
Burger, Corinna et al.; "Recombinant AAV Viral Vectors Pseudotyped with Viral Capsids from Serotypes 1, 2, and 5 Display Differential Efficiencey and Cell Tropism after Delivery to different Regions of the Central Nervous System;" Molecular Therapy, vol. 10, No. 2, Aug. 2004; pp. 302-317.
Cabin, Deborah et al.; "Exacerbated synucleinopathy in mice expressing A53T SNCA on a SNCA null background;" Neurobiology of Aging 26 (2005) 25-35.
Chamberlin, Nancy et al.; "Recombinant adeno-associated virus vector: use for transgene expression and anterograde tract tracing in the CNS;" Brain Research 793 (1998) 169-175.
Chartier-Harlin, Marie-Christine et al.; "α-synuclein locus duplication as a cause of familial Parkinson's disease;" Lancet 2004; 364: 1167-69.
Chen, Li et al.; "α-Synuclein phosphorylation controls neurotoxicity and inclusion formation in a *Drosophila* model of Parkinson disease;" Nature Neuroscience, vol. 8, No. 5, May 2005.
Choi, Hyung et al.; "Immortalization of embryonic mesencephalic dopaminergic neurons by somatic cell fusion;" *Brain Research*, 552 (1991) 67-76.
Chung, Kenny; "New insights into Parkinson's disease;" J Neurol (2003) 250 [Suppl 3]: III/15-III/24.
Connor, B. et al.; Differential effects of glial cell line-derived neurotrophic factor (GDNF) in the striatum and substantia nigra of the age Parkinsonian rat; Gene Therapy (1999) 6, 1936-1951.
Daly, Thomas; "Overview of Adeno-Associated Viral Vectors;" Methods in Molecular Biology, vol. 246: Gene Delivery to Mammalian Cells: vol. 2: Viral Gene Transfer Techniques.
Dauer, William et al.; "Resistance of α-synuclein null mice to the parkinsonian neurotoxin MPTP;" 14524-14529; PNAS; Oct. 29, 2002; vol. 99, No. 22.
Davidson, Beverly et al.; "Viral Vectors for Gene Delivery to the Nervous System;" Nature Reviews; Neuroscience; vol. 4; May 2003; pp. 353-364.
Davidson, Beverly et al.; "Molecular medecine for the brain: silencing of disease genes with RNA interference;" The Lancet; Neurology; vol. 3 Mar. 2004; pp. 145-149.
Elbashir, Sayda et al.; "Duplexes of 21-nucleotide RNAs mediate RNA interference in cultured mammalian cells;" Nature, vol. 411; May 24, 2001; pp. 494-498.

(Continued)

*Primary Examiner* — Jennifer Pitrak McDonald
(74) *Attorney, Agent, or Firm* — Brinks Hofer Gilson & Lione

(57) ABSTRACT

The present invention is directed to small interfering RNAs that down regulate expression of a synuclein gene and methods of using the small interfering RNAs.

17 Claims, No Drawings

OTHER PUBLICATIONS

Elbashir et al.; "Fuctional Anatomy of siRNAs for Mediating Efficient RNAI in *Drosophila melanogaster* Embryo Lysate"; The EMBO Journal, v.20(23):6877-6888.

Erikson, Jason et al.; "Caught in the Act: α-synuclein Is the Culprit in Parkinson's Disease;" Neuron, vol. 40; pp. 453-456, Oct. 30, 2003.

Erikson, Jason et al.; "Molecular Pathogenesis of Parkinson Disease;" Arch Neurol. 2005; 62:353-357.

Feany, Mel et al.; "A *Drosophila* model of Parkinson's disease;" Nature, vol. 404; Mar. 23, 2000.

Fernagut, Pierre-Olivier et al.; "Alpha-synuclein and transgenic mouse models;" Neurobiology of Disease 17 (2004); pp. 123-130.

Fire, Andrew et al.; "Potent and specific genetic interference by double-stranded RNA in *Caenorhabditis elegans*;" Nature, vol. 391; Feb. 19, 1998; pp. 806-811.

Fornai, Francesco et al.; "Occurrence of neuronal inclusions combined with increased nigral expression of α-synuclein within dopaminergic neurons following treatment with amphetamine derivatives in mice;" Brain Research Bulletin 65 (2005); pp. 405-413.

Fornai, Francesco et al.; "Parkinson-like syndrome induced by continuous MPTP infusion: Convergent roles of the ubiquitin-proteasome system and α-synuclein;" PNAS; Mar. 1, 2005; vol. 102, No. 9; pp. 3413-3418.

Gispert, Suzana et al.; "Transgenic mice expressing mutant A53T human alpha-synuclein show neuronal dysfunction in the absence of aggregate formation;" Molecular and Cellular Neuroscience 24 (2003); pp. 419-429.

Goedert, Michel; "Alpha-Synuclein and Neurodegenerative Diseases;" Nature; Jul. 2001; vol. 2; pp. 492-501.

Gomez-Isla, Teresa et al.; "Motor dysfunction and gliosis with preserved dopaminergic markers in human α-synuclein A30P transgenic mice;" Neurobiology of Aging 24 (2003); pp. 245-258.

Gómez-Santos, Cristina et al.; "MIPP+ increases α-synuclein expression and ERK/MAP-kinase phosphorylation in human neuroblastoma SH-SY5Y cells;" Brain Research 935 (2002) 32-39.

Gonzalez-Alegre, M.D., Pedro et al.; "Toward Therapy for DYT1 Dystonia: Allele-Specific Silencing of Mutant TorsinA;" Ann Neurol 2003; 53:781-787.

Grazia Spillantini, Maria et al.; "α-synuclein in filamentous inclusions of Lewy bodies from Parkinson's disease and dementia with Lewy bodies;" *Proc. Natl. Acad. Sci. USA*; vol. 95; pp. 6469-6473; May 1998.

Greenamyre, J. Timothy et al.; "Parkinson's—Divergent Causes, Convergent Mechanisms;" Science, vol. 304; May 21, 2004.

Hannon, Gregory; "RNA interference;" Nature, vol. 418; Jul. 11, 2002; 244-251; XP-002979088.

Hashimoto, Makoto et al.; "Transgenic Models of α-synuclein Pathology Past, Present, and Future;" Ann. N.Y. Acad. Sci. 991: 171-188 (2003).

Iwai, Akihiko et al.; "The Precursor Protein of Non-Aβ Component of Alzheimer's Disease Amyloid is a Presynaptic Protein of the Central Nervous System;" Neuron, vol. 14, pp. 467-475; Feb. 1995.

Jiang, L. et al.; "Tight regulation from a single tet-off rAAV vector as demonstrated by flow cytometry and quantitative, real-time PCR;" Gene Therapy (2004) 11; pp. 1057-1067.

Kahle, Philipp J. et al.; "Physiology and Pathophysiology of α-synuclein Cell Culture and Transgenic Animal Models Based on a Parkinson's Disease-associated Protein;" Annals of New York Academy of Sciences—Kahle et al.: Physiology & Pathophysiology of α-synuclein; pp. 33-41.

Kahle, Phillipp J. et al.; Subcellular Localization of Wild-Type and Parkinson's Disease-Associated Mutant α-synuclein in Human and Transgenic Mouse Brain; The Journal of Neuroscience; Sep. 1, 2000; 20(17):6365-6373.

Kaludov, Nikola et al.; "Scalable Purification of Adeno-Associated Virus Type 2, 4, or 5 Using Ion-Exchange Chromatography;" Human Gene Therapy 13:1235-1243 (Jul. 1, 2002).

Kaplitt, Michael et al.; "Preproenkephalin promoter yields region-specific and long-term expression in adult brain after direct in vivo gene transfer via a defective herpes simplex viral vector;" *Proc. Natl. Acad. Sci. USA*; vol. 91, pp. 8979-8983; Sep. 1994.

Kirik, Deniz et al.; "Nigrostriatal α-synucleinopathy induced by viral vector-mediated overexpression of human α-synuclein: A new primate model of Parkinson's disease;" PNAS, Mar. 4, 2003; vol. 100, No. 5; pp. 2884-2889.

Kink, Deniz et al.; "Parkinson-Like Neurodegeneration Induced by Targeted Overexpression of α-synuclein in the Nigrostriatal System;" The Journal of Neuroscience; Apr. 1, 2002; 22(7):2780-2791.

Klein, Ronald et al.; "Dopaminergic Cell Loss Induced by Human A30P α-synuclein Gene Transfer to the Rat Substantia Nigra;" Human Gene Therapy 13:605-612; Mar. 20, 2002.

Kowall, Neil et al.; "MPTP induces alpha-synuclein aggregation in the substantia nigra of baboons;" Neuroreport, vol. 11(1); Jan. 17, 2002; 211-213.

Kozlowski, D.A. et al.; "Real-Time RT-PCR Analysis of mRNAs for GDNF and Neurturin Receptors (GFRα1 and GFRα2) in Striatum and Substantia Nigra (SN) of Normal and 6-OHDA Lesioned Rats;" http://sfn.Scholarone.com/itin2000/main.html?new_page_id=76&abstract_id=14929&is_tech=06/11/2007 1:55:18 PM; Abstract.

Kozlowski, Dorothy et al.; "Quantitative Analysis of Transgene Protein, mRNA, and Vector DNA Following Injection of an Adenoviral Vector Harboring Glial Cell Line-Derived Neurotrophic Factor into the Primate Caudate Nucleus;" Molecular Therapy vol. 3, No. 2; Feb. 2001; pp. 256-261.

Kozlowski, Dorothy et al.; "Delivery of a GDNF Gene into the Substantial Nigra after a Progressive 6-OHDA Lesion Maintains Functional Nigrostriatal Connections;" Experimental Neurology 166, 1-15 (2000).

Kozlowski, Dorothy et al.; "Quantitative Analyses of GFRα-1 and GFRα-2 mRNAs and tyrosine hydroxylase protein in the nigrostriatal system reveal bilateral compensatory changes following unilateral 6-OHDA lesions in the rat;" Brain Research 1016 (2004); pp. 170-181.

Krüger, Rejko et al.; "Ala30Pro mutation in the gene encoding α-synuclein in Parkinson's disease;" nature genetics vol. 18; Feb. 1998; pp. 106-108.

Lakso, Merja et al.; "Dopaminergic neuronal loss and motor deficits in *Caenorhabditis elegans* overexpressing human α-synuclein;" *Journal of Neurochemistry*, 2003; 86, pp. 165-172.

Lee, Michael et al.; "Human α-synuclein-harboring familial Parkinson's disease-linked Ala-53 →Thr mutation causes neurodegerative disease with α-synuclein aggregation in transgenic mice;" PNAS; Jun. 25, 2002, vol. 99, No. 13; pp. 8968-8973.

Lindersson, Evo et al.; "Proteasomal Inhibition by α-synuclein Filaments and Oligomers;" The Journal of Biological Chemistry; vol. 279, No. 13; Issue of Mar. 26, pp. 12924-12934; 2004.

Lo Bianco, C. et al.; "α-Synucleinopathy and selective dopaminergic neuron loss in a rat lentiviral-based model of Parkinson's disease;" PNAS, Aug. 6, 2003; vol. 99, No. 16; pp. 10813-10818.

Lu, Yan-Yan et al.; "Intramuscular injection of AAV-GDNF results in sustained expression of transgenic GDNF, and its delivery to spinal motoneurons by retrograde transport;" Neuroscience Research 45 (2003) 33-40.

Maguire-Zeiss, Kathleen et al.; "Synuclein, dopamine and oxidative stress: co-conspirators in Parkinson's disease?;" Molecular Brain Research 134 (2005) 18-23.

Martí, Maria et al.; "Clinical Overview of the Synucleinopathies;" *Movement Disorders*, vol. 18, Suppl. 6; 2003; pp. S21-S27.

Masliah, Eliezer et al.; "Dopaminergic Loss and Inclusion Body Formation in α-synuclein Mice: Implications for Neurodegenerative Disorders;" Science, vol. 287; Feb. 18, 2000; pp. 1265-1269.

Matsuoka, Yasuji et al.; "Lack of Nigral Pathology in Transgenic Mice Expressing Human α-Synuclein Driven by the Tyrosine Hydroxylase Promoter;" *Neurobiology of Disease* 8; pp. 535-539; 2001.

McCarty, Douglas et al.; "Integration of Adeno-Associated Virus (AAV) and Recombinant AAV Vectors;" Annu. Rev. Genet. 2004; 38:819-45.

McManus, Michael et al.; "Gene Silencing in Mammals by Small Interfering RNAs;" Nature Reviews/Genetics; vol. 3; Oct. 2002; pp. 737-747.

Miller, D.W. et al.; "α-Synuclein in blood and brain from familial Parkinson disease with *SNCA* locus triplication;" Neurology 62; May (2 of 2) 2004; 1835-1838.

Miller, Victor et al.; "Targeting Alzheimer's disease genes with RNA interference: an efficient strategy for silencing mutant alleles;" Nucleic Acids Research; 2004; vol. 32, No. 2; pp. 661-668.

Miller, Victor et al.; "Allele-specific silencing of dominant disease genes;" PNAS, vol. 100, No. 12; Jun. 10, 2003; pp. 7195-7200.

Miwa, Hideto et al.; "Retrograde dopaminergic neuron degeneration following intrastriatal proteasome inhibition;" Neuroscience Letters 380 (2005); pp. 93-98.

Nakai, Hiroyuki et al.; "AAV serotype 2 vectors preferentialy integrate into active genes in mice;" Nature Genetics; vol. 34, No. 3; Jul. 2003; pp. 297-302.

Nelson, P.T. et al.; "The mRNA of α-synuclein is a Putative MicroRNA (miRNA) Target;" Program No. 558.8; *2003 Abstract Viewer/Itinerary Planner*, Washington, D.C.: Society for Neuroscience, 2003; XP-001181837; Abstract.

Neumann, Manuela et al.; "Misfolded proteinase K-resistant hyperphosphorylated α-synuclein in aged transgenic mice with locomotor deterioration and in human α-synucleinopathies;" The Journal of Clinical Investigation; Nov. 2002; vol. 110; No. 10; pp. 1429-1439.

Paterna, Jean-Charles et al.; "Transduction Profiles of Recombinant Adeno-Associated Virus Vectors Derived from Serotypes 2 adn 5 in the Nigrostriatal System of Rats;" Journal of Virology, Jul. 2004; pp. 6808-6817.

Payton, Jacqueline et al.; "Structural Determinants of PLD2 Inhibition by α-Synuclein;" J. Mol. Biol.; (2004) 337; pp. 1001-1009.

Perez, Ruth et al.; "Could a loss of α-synuclein function put dopaminergic neurons at risk?;" Journal of Neurochemistry, 2004; 89, pp. 1318-1324.

Polymeropoulos, Mihael et al.; "Mutation in the α-Synuclein Gene Identified in Families with Parkinson's Disease;" Science; vol. 276; Jun. 27, 1997; pp. 2045-2047.

Raghavan, Ravi et al.; "Alpha-Synuclein Expression in the Developing Human Brain;" Pediatric and Developmental Pathology 7; pp. 506-516; 2004.

Recchia, Alessandra et al.; "α-Synuclein and Parkinson's disease;" The FASEB Journal; vol. 18; Apr. 2004.

Richfield, Eric et al.; "Behavioral and Neurochemical Effects of Wild-Type and Mutated Human α-Synuclein in Transgenic Mice;" Experimental Neurology 175; 35-48 (2002).

Robertson, H.A. et al.; "$D_1$—dopamine receptor agonists selectively activate strial c-*fos* independent of rotational behaviour;" Brain Research, 503 (1989); pp. 346-349.

Rockenstein, Edward et al.; "Differential Neuropathological Alterations in Transgenic Mice Expressing α-Synuclein From the Platelet-derived Growth Factor and Thy-1 Promoters;" Journal of Neuroscience Research 68:568-578 (2002).

Rockenstein, Edward et al.; "Lysosomal Pathology Associated With α-Synuclein Accumulation in Transgenic Models Using an eGFP Fusion Protein;" Journal of Neuroscience Research 80:247-259 (2005).

Rubinson, Douglas et al.; "A lentivirus-based system to functionally silence genes in primary mammalian cells, stem cells and transgenic mice by RNA interference;" Nature Genetics, vol. 33; Mar. 2003.

Sapru, M.K. et al.; "Small Interfering RNA (siRNA)-Mediated Silencing of α-Synuclein Gene Expression;" Program No. 297.9 *2003 Abstract Viewer/Itinerary Planner*; Washington, D.C.: Society for Neuroscience, 2003; Abstract.

Sapru, Mohan et al.; "Silencing of Endogenous Human α-Synuclein by a Lentiviral Vector Expressing Short Hairpin RNA;" Molecular Therapy, vol. 11, Supplement 1, May 2005; Abstract.

Sapru, Mohan et al.; "Silencing of human α-Synuclein in vitro and in rat brain using lentiviral-mediated RNAi;" Experimental Neurology 198 (2006); pp. 382-390.

Sapru, Mohan et al.; "Small Interfering RNA (siRNA)-Mediated Silencing of α-synuclein Gene Expression;" Society for Neuroscience Annual Meeting; New Orleans; 2003.

Sapru, M.K. et al.; "Vector-Based RNA Interference Mediates Highly Potent Silencing of Human α-Synuclein Gene Expression;" Society for Neuroscience Annual Meeting; 2004.

Schapira, Anthony; "Disease Modification in Parkinson's Disease;" The Lancet—Neurology, vol. 3; Jun. 2004.

Semizarov, Dimitri et al.; "Specificity of short interfering RNA determined through gene expression signatures;" PNAS; May 27, 2003; vol. 100; No. 11; pp. 6347-6352.

Sherer, Todd et al.; "Subcutaneous Rotenone Exposure Causes Highly Selective Dopaminergic Degeneration and α-Synuclein Aggregation;" Experimental Neurology 179, 9-16 (2003).

Sioud, Mouldy et al.; "Cationic liposome-mediated delivery of siRNAs in adult mice;" Biochemical and Biophysical Research Communications 312; (2003); pp. 1220-1225.

Singleton, A.B. et al.; "α-Synuclein Locus Triplication Causes Parkinson's Disease;" Science; vol. 302; Oct. 31, 2003; pp. 841; XP-002382468.

Smith, Richard et al.; "Serum-free production and column purification of adeno-associated virus type 5;" Journal of Virological Methods; 114 (2003); pp. 115-124.

Snyder, Heather et al.; "Aggregated and Monomeric α-Synuclein Bind to the S6' Proteasomal Protein and Inhibit Proteasomal Function;" The Journal of Biological Chemistry, vol. 278, No. 14; Issue of Apr. 4, pp. 11753-11759; 2003.

St. P. McNaught, Kevin et al.; "Altered Proteasomal Function in Sporadic Parkinson's Disease;" Experimental Neurology 179; pp. 38-46; 2003.

St. P. McNaught, Ph.D., Kevin et al.; "Proteolytic Stress: A Unifying Concept for the Etiopathogenesis of Parkinson's Disease;" Ann Neurol 2003;53 (suppl 3):S73-S86.

St. P. McNaught, Kevin et al.; "Failure of the ubiquitin-proteasome system in Parkinson's disease;" Nature Reviews/Neuroscience; vol. 2; Aug. 2001; pp. 589-594.

St. P. McNaught, Kevin et al.; "Systemic Exposure to Proteasome Inhibitors Causes a Progressive Model of Parkinson's Disease;" Ann Neurol 2004; 56:149-162.

Takahashi, Tetsuya et al.; "Identification and Characterization of a Novel Pyk2/Related Adhesion Focal Tyrosine Kinase-associated Protein That Inhibits α-Synuclein Phosphorylation;" The Journal of Biological Chemistry; vol. 278; No. 43; Issue of Oct. 24; pp. 42225-42233; 2003.

Tanaka, Yuji et al.; "Inducible expression of mutant α-Synuclein decreases proteasome activity and increases sensitivity to mitochondria-dependent apoptosis;" Human Molecular Genetics; 2001; vol. 10, No. 9; pp. 919-926.

Tenenbaum, I. et al.; "Recombinant AAV-mediated gene delivery to the central nervous system;" The Journal of Gene Medicine; 2004; 6: S212-S222.

Thakker, Deepak et al.; "Neurochemical and behavioral consequences of widespread gene knockdown in the adult mouse brain by using nonviral RNA interference;" PNAS; Dec. 7, 2004, vol. 101; No. 49; pp. 17270-17275.

Thiruchelvam, M.J. et al.; "Risk factors for dopaminergic neuron loss in human α-Synuclein transgenic mice;" European Journal of Neuroscience; vol. 19; pp. 845-854; 2004.

Urabe, Masashi et al.; "Insect Cells as a Factory to Produce Adeno-Associated Virus Type 2 Vectors;" Human Gene Therapy 13:1935-1943 (Nov. 1, 2002).

Van der Putten, Herman et al.; "Neuropathology in Mice Expressing Human α-Synuclein;" The Journal of Neuroscience; Aug. 15, 2000 ;20(16):6021-6029.

Vila, Miguel et al.; "α-Synuclein Up-Regulation in Substantia Nigra Dopaminergic Neurons Following Administration of the Parkinsonian Toxin MPTP;" Journal of Neurochemistry, vol. 74, No. 2; 2000; pp. 721-729.

Watabe, Masahiko et al.; "Rotenone Induces Apoptosis via Activation of Bad in Human Dopaminergic SH-SY5Y Cells;" The Journal of Pharmacology and Experimental Therapeutics; vol. 311, No. 3; pp. 948-953.

Webb, Julie et al.; "α-Synuclein is Degraded by both Autophagy and the Proteasome;" The Journal of Biological Chemistry; vol. 278, No. 27; Issue of Jul. 4; pp. 25009-25013; 2003.

Xia, Haibin et al.; "siRNA-mediated gene silencing in vitro and in vivo;" Nature biotechnology; vol. 20; Oct. 2002; pp. 1006-1010.

Xia, Haibin et al.; "RNAi suppresses polyglutamine-induced neurodegeneration in a model of spinocerebellar ataxia;" nature medicine; vol. 10, No. 8; Aug. 2004; pp. 816-820.

Zarranz, Juan et al.; "The New Mutation, E46K, of α-Synuclein Causes Parkinson and Lewy Body Dementia;" Ann Neurol 2004; 55:164-173.

Zolotukhin, Sergei et al.; "Production and purification of serotype 1, 2, and 5 recombinant adeno-associated viral vectors;" Methods 28 (2002); pp. 158-167.

International Search Report mailed Sep. 29, 2006 for International Application No. PCT/US2005/034516.

Agami; "RNAi and related mechanisms and their potential use for therapy"; Current Opinion in Chemical Biology vol. 6; pp. 829-834; 2002.

Holen et al.; "Positional effects of short interfering RNAs targeting the human coagulation trigger Tissue Factor"; Nucleic Acids Research, vol. 30, No. 8; 2002; pp. 1757-1766.

* cited by examiner

SIRNA-MEDIATED GENE SILENCING OF SYNUCLEIN

This application is a divisional application of U.S. application Ser. No. 11/726,211, filed Mar. 21, 2007 now abandoned, which is a continuation-in-part of International Application No. PCT/US2005/034516, filed Sep. 27, 2005, which claims the benefit of U.S. Provisional Application Ser. No. 60/614,112, filed Sep. 29, 2004, these references are incorporated herein in their entirety.

FEDERALLY SPONSORED RESEARCH OR DEVELOPMENT

This invention was made with support under Grant No. NS31957 awarded by the National Institutes of Health. The government may have certain rights in this invention.

FIELD OF THE INVENTION

The present invention generally relates to methods and systems for siRNA gene silencing and more specifically relates to methods and systems for siRNA gene silencing of the α-synuclein gene and synuclein gene family members.

BACKGROUND

RNA interference (RNAi) refers to the process of sequence-specific post transcriptional gene silencing mediated by small interfering RNAs (siRNA) (Fire et al., 1998, *Nature*, 391, 806-11). Long double stranded RNA (dsRNA) in cells stimulates the activity of a ribonuclease III enzyme referred to as dicer. Dicer is involved in the processing of the long dsRNA into short pieces of siRNA (Bernstein et al., 2001, *Nature*, 409, 363-6). siRNAs derived from dicer activity are typically about 21-23 nucleotides in length and include duplexes of about 19 base pairs.

The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, *Nature*, 411, 494-498).

siRNA mediated RNAi has been studied in a variety of systems. Recent work in *Drosophila* embryonic lysates has revealed certain requirements for siRNA length, structure, chemical composition, and sequence that are essential to mediate efficient RNAi activity (Elbashir et al., 2001, *EMBO J.*, 20, 6877-88). RNAi technology has been used in mammalian cell culture, where a siRNA-mediated reduction in gene expression has been accomplished by transfecting cells with synthetic RNA oligonucleotides (Caplen et al., 2001, *Proc. Natl. Acad. Sci., U.S.A.*, 98, 9742-7; Elbashir et al., 2001, *Nature*, 411, 494-8). The ability to use siRNA-mediated gene silencing in mammalian cells combined with the high degree of sequence specificity allows RNAi technology to be used to selectively silence expression of mutant alleles or toxic gene products in dominantly inherited diseases, including neurodegenerative diseases. Several neurodegenerative diseases, such as Parkinson's disease, Alzheimer's disease, Huntington's disease, Spinocerebellar Ataxia Type 1, Type 2, and Type 3, and dentatorubral pallidoluysian atrophy (DRLPA), have proteins identified that are involved in the overall pathogenic progression of the disease.

siRNA-mediated gene silencing of mutant forms of human ataxin-3, Tau and TorsinA, genes which cause neurodegenerative diseases such as spinocerebellar ataxia type 3, frontotemporal dementi and DYT1 dystonia respectively, has been demonstrated in cultured cells (Miller et al. 2003, *Proc. Natl. Acad. Sci., U.S.A.*, 100, 7195-7200; Gouzales-Alegre et al., 2003, *Ann. Neurol.* 53, 781-7).

α-synuclein (α-syn) is involved in the pathogenesis of neurodegenerative diseases including Parkinson's disease (PD), dementia with Lewy bodies (DLB), the Lewy body variant of Alzheimer's disease (LBVAD), multiple systems atrophy (MSA), and neurodegeneration with brain iron accumulation type-1 (NBIA-1), as well as sleep and other disorders. Common to all of these diseases, termed synucleinopathies, are proteinaceous insoluble inclusions in the neurons and the glia which are composed primarily of α-syn.

α-syn is part of a large family of proteins including β- and γ-synuclein and synoretin. α-syn is expressed in the normal state associated with synapses and plays a role in neural plasticity, learning and memory. Mutations in the human α-syn (h-α-syn) gene that enhance the aggregation of α-syn have been identified (alanine to threonine substitution at position 53 (A53T) and alanine to proline at position 30 (A30) and are associated with rare forms of autosomal dominant forms of PD. Altered h-α-syn function triggers neurodegenerative processes associated with PD such as the selective loss of dopaminergic neurons in the substantia nigra pars compacta leading to substantial depletion of dopamine in the striatum resulting in severe motor impairment (Dawson et al., 2002, *Nat. Neurosci.*, November; 5 Suppl: 1058-61). Abnormal accumulation of wild-type or mutant α-syn impairs proteasome function, interferes with vesicular dopamine storage, renders endogenous dopamine toxic, and contributes to mitochondrial dysfunction (Polymeropoulos, M., 2000, *Ann. NY. Acad. Sci.*, 920, 28-32, Lotharius et al., 2002, *Nature Reviews Neurosci.* 3, 932-42).

A need exists for a siRNA-mediated gene silencing methods and systems for silencing α-syn and its family members.

BRIEF SUMMARY

In one aspect of the present invention, a small interfering RNA (siRNA) that down regulates expression of a synuclein gene is provided.

In another aspect of the present invention, a composition is provided that includes a siRNA in an amount sufficient to down regulate expression of a synuclein gene, wherein the siRNA comprises a nucleotide sequence substantially complementary to 15-30 consecutive nucleotides of SEQ ID NO: 1.

In yet another aspect of the present invention, a vector is provided that includes a promoter and a nucleotide sequence operatively linked to the promoter which comprises 15-30 consecutive nucleotides of SEQ ID NO: 1 wherein the nucleotide sequence encodes a siRNA that down regulates a synuclein gene.

In another aspect of the present invention, a method of reducing expression of a synuclein gene in a cell is provided. The method includes introducing into a cell a siRNA in an amount effective to down regulate expression of the synuclein gene. The siRNA includes a nucleotide sequence substantially complementary to 15-30 consecutive nucleotides of SEQ ID NO: 1.

In yet another aspect of the present invention, a method of reducing cell death is provided. The method includes introducing into a cell a siRNA in an amount effective to down regulate expression of the synuclein gene. The siRNA includes a nucleotide sequence substantially complementary to 15-30 consecutive nucleotides of SEQ ID NO: 1.

In another aspect of the present invention, a method of treating a neurodegenerative disease or a synucleinopathy in a subject is provided. The method includes administering to the subject a therapeutically effective amount of a siRNA comprising a nucleotide sequence substantially complementary to 15-30 consecutive nucleotides of SEQ ID NO: 1 wherein the expression of the synuclein gene is down regulated.

Advantages of the present invention will become more apparent to those skilled in the art from the following description of the preferred embodiments of the present invention that have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE PRESENTLY PREFERRED EMBODIMENTS

The present invention utilizes siRNA-mediated gene silencing for silencing the synuclein family of genes.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijssen, ed.); Fundamental Virology, 2nd Edition, vol. I & II (B. N. Fields and D. M. Knipe, eds.)

DEFINITIONS

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides, conservatively modified variants thereof, complementary sequences, and degenerate codon substitutions that have similar binding properties as the reference nucleic acid and are metabolized in a manner similar to naturally occurring nucleotides.

The terms "nucleic acid," "nucleic acid molecule," "nucleic acid fragment," "nucleic acid sequence or segment," or "polynucleotide" are used interchangeably.

The term "gene" is used broadly to refer to any segment of nucleic acid associated with a biological function. Thus, genes include coding sequences and/or the regulatory sequences required for their expression. For example, the term "gene" refers to a nucleic acid fragment that expresses mRNA, functional RNA, or specific protein, including regulatory sequences. The term "genes" also includes non-expressed DNA segments that, for example, form recognition sequences for other proteins. "Genes" can be obtained from a variety of sources, including cloning from a source of interest or synthesizing from known or predicted sequence information, and may include sequences designed to have desired parameters.

The term "gene delivery" or "gene transfer" refers to methods or systems for reliably inserting foreign nucleic acids into target cells, such as into cells of the central and peripheral nervous systems. Such methods can result in transient or long term expression of genes. Gene transfer provides a method for the treatment of acquired and inherited diseases.

The term "vector" refers to any genetic element, such as a plasmid, phage, transposon, cosmid, chromosome, virus, virion, etc., which is capable of replication when associated with the proper control elements, such as a helper virus, and which can transfer gene sequences between cells. Thus, the term includes cloning and expression vehicles, as well as replication-defective viral vectors. Numerous types of vectors exist and are well known in the art.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "operatively linked" means that a selected nucleic acid sequence, e.g., encoding a siRNA construct is in proximity with a promoter to allow the promoter to regulate expression of the selected nucleic acid sequence. In general, the promoter is located upstream of the selected nucleic acid sequence in terms of the direction of transcription and translation.

The term "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least about 40%, 50%, 60%, 70%, 80%, 90%, 95%, 96%, 97%, 98%, to 99% sequence identity to the native (endogenous) nucleotide sequence.

The term "conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The term "transfection" is used to refer to the uptake of foreign nucleic acids by a mammalian cell. A cell has been "transfected" when an exogenous nucleic acid has been introduced inside the cell membrane. Transfection can be used to introduce one or more exogenous nucleic acid moieties, such as a plasmid vector and other nucleic acid molecules, into suitable cells. The term refers to both stable and transient uptake of the genetic material.

The term "transduction" refers to the delivery of a nucleic acid molecule to a recipient cell either in vivo or in vitro, via a viral vector.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

The term "down regulated," as it refers to genes inhibited by the subject RNAi method, refers to a diminishment in the level of expression of a gene(s) in the presence of one or more siRNA construct(s) when compared to the level in the absence of such siRNA construct(s). The term "down regulated" is used herein to indicate that the target gene expression is lowered by 1-100%. For example, the expression may be reduced by about 10, 20, 30, 40, 50, 60, 70, 80, 90, 95, or 99%.

The term "gene silencing" refers to the suppression of gene expression, e.g., transgene, heterologous gene and/or endogenous gene expression. Gene silencing may be mediated through processes that affect transcription and/or through processes that affect post-transcriptional mechanisms. Gene silencing may occur when siRNA initiates the degradation of the mRNA of a gene of interest in a sequence-specific manner via RNA interference (for a review, see Brantl, 2002, *Biochim. Biophys. Acta*, 1575(1-3): 15-25). Gene silencing may be allele-specific wherein specific silencing of one allele of a gene occurs.

The term "RNA interference (RNAi)" refers to the process of sequence-specific, posttranscriptional gene silencing initiated by siRNA. During RNAi, siRNA induces degradation of target mRNA with consequent sequence-specific inhibition of gene expression.

The term "small interfering" or "short interfering RNA" or "siRNA" refers to a nucleic acid that forms a double stranded RNA, which double stranded RNA has the ability to reduce or inhibit expression of a gene or target gene when the siRNA is expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. siRNA is "targeted" to a gene in that the nucleotide sequence of the duplex portion of the siRNA is substantially complementary to a nucleotide sequence of the targeted gene. The siRNA sequence duplex needs to be of sufficient length to bring the siRNA and target RNA together through complementary base-pairing interactions. The siRNA of the invention may be of varying lengths. The length of the siRNA is preferably greater than or equal to ten nucleotides and of sufficient length to stably interact with the target RNA; specifically 10-30 nucleotides; more specifically any integer between 10 and 30 nucleotides, such as 10, 11, 12, 13, 14, 15, 16, 17, 18, 19, 20, 21, 22, 23, 24, 25, 26, 27, 28, 29, and 30. By "sufficient length" is meant a nucleotide of greater than or equal to 10 nucleotides that is of a length great enough to provide the intended function under the expected condition. The term "stably interact" refers to interaction of the small interfering RNA with target nucleic acid (e.g., by forming hydrogen bonds with complementary nucleotides in the target under physiological conditions).

The siRNA may be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal. The RNA duplex of the siRNA may be constructed in vitro using synthetic oligonucleotides.

The term "inverted repeat" refers to a nucleic acid sequence comprising a sense and an antisense element positioned so that they are able to form a double stranded siRNA when the repeat is transcribed. The inverted repeat may optionally include a linker or a heterologous sequence between the two elements of the repeat. The elements of the inverted repeat have a length sufficient to form a double stranded RNA. Typically, each element of the inverted repeat is about 15 to about 100 nucleotides in length, preferably about 20-30 base nucleotides, preferably about 20-25 or 24-29 nucleotides in length, e.g., 20, 21, 22, 23, 24, 25, 26, 27, 28, 29, or 30 nucleotides in length.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, 91%, 92%, 93%, 94%, 95%, 96%, 97%, 98% or 99% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence, such as an RNA nucleotide complementary to a DNA nucleotide. Preferably, the substantial identity exists over a region that is at least about 6-7 amino acids or 25 nucleotides in length.

An example of an algorithm that is suitable for determining percent sequence identity and sequence similarity is the BLAST algorithm, which is described in Altschul et al., 1977, *Nuc. Acids Res.* 25:3389-3402. BLAST is used, with the parameters described herein, to determine percent sequence identity for the nucleic acids and proteins of the invention. Software for performing BLAST analysis is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA,* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "therapeutically effective amount" refers to an amount of nucleic acid product that is nontoxic but sufficient to provide the desired effect and performance at a reasonable benefit/risk ratio attending any medical treatment.

The term "treating" refers to ameliorating at least one symptom of a disease or a condition.

The terms "neurodegenerative disease" and "neurodegenerative disorder" refer to both hereditary and sporadic conditions that are characterized by nervous system dysfunction, and which may be associated with atrophy of the affected central or peripheral nervous system structures, or loss of function without atrophy. Neurodegenerative diseases and disorders include but are not limited to amyotrophic lateral sclerosis (ALS), hereditary spastic hemiplegia, primary lateral sclerosis, spinal muscular atrophy, Kennedy's disease, Alzheimer's disease, Parkinson's disease, synucleinopathies, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCAT, SCA2, SCA3, SCA6, SCAT), spinal and bulbar muscular atrophy (SBMA), and dentatorubropallidoluysian atrophy (DRPLA).

The term "synucleinopathies" refers to conditions that are characterized by proteinaceous insoluble inclusions in the neurons and the glia which are composed primarily of α-synuclein. Synucleinopathies include several neurodegenerative diseases such as Parkinson's disease (PD), dementia with Lewy bodies (DLB), the Lewy body variant of Alzheimer's disease (LBVAD), multiple systems atrophy (MSA), and neurodegeneration with brain iron accumulation type-1 (NBIA-1). Synucleinopathies also may include disorders such as sleep disorders, some rapid eye movement disorders, such as idiopathic rapid eye movement sleep behavior disorder (RBD), and other disorders known to one of skill in the art.

Isolated siRNA Molecules

Various siRNA agents may be used to modulate the activity and/or expression of a synuclein gene family member in a cell. The synuclein gene family may include α-synuclein, β-synuclein, γ-synuclein and synoretin, and mutants and variants thereof. By way of example, α-synuclein nucleotides and polypeptides will be discussed. One of skill in the art will understand that the present invention is not limited to α-synuclein and may include all synuclein family members from any vertebrate, preferably mammalian, source.

The full nucleotide sequence encoding human α-synuclein is provided in SEQ ID NO: 1. The h-α-syn polypeptide is provided in SEQ ID NO: 2. Two variants of the h-α-syn sequence are provided in SEQ ID NO: 3 and SEQ ID NO: 4. In SEQ ID NO: 3, a guanine residue is substituted with a cytosine residue at position 134 in SEQ ID NO: 1, resulting in an alanine to proline substitution at amino acid 30 (A30P) of SEQ ID NO: 2 and in SEQ ID NO: 4, a guanine residue is substituted with an adenosine residue at nucleotide 203 of SEQ ID NO: 1, resulting in an alanine to threonine substitution at amino acid 53 (A53T) of SEQ ID NO: 2. The α-syn cDNA is provided in SEQ ID NO: 5. The siRNA of the present invention may be used to down regulate any of the synuclein family of genes.

In accordance with the present invention, siRNA specific against synuclein mRNA produced in a cell may be used to down-regulate the expression of the synuclein gene. As will be described in more detail below, the siRNA may be directed to down regulating expression of wild-type α-syn, the A30P mutant, and/or the A53T mutant as well as the other synuclein family members. The siRNAs may be designed to target a specific region of the synuclein gene, for example, by selecting regions of the synuclein gene. Generally, a target sequence on the target mRNA can be selected from a given cDNA sequence corresponding to the target mRNA, preferably beginning 50 to 100 nucleotides downstream (i.e., in the 3' direction) from the start codon. The target sequence can, however, be located in the 5' or 3' untranslated regions, or in the region nearby the start codon. Preferably, target sequences have approximately 50% G/C content. Highly G-rich sequences are preferably avoided because they tend to form G-quartet structures.

siRNAs may be constructed in vitro using synthetic oligonucleotides or appropriate transcription enzymes or in vivo using appropriate transcription enzymes or expression vectors. The siRNAs include a sense RNA strand and a complementary antisense RNA strand annealed together by standard Watson-Crick base-pairing interactions to form the base pairs. The sense and antisense strands of the present siRNA may be complementary single stranded RNA molecules to form a double stranded (ds) siRNA or a DNA polynucleotide encoding two complementary portions that may include a hairpin structure linking the complementary base pairs to form the siRNA. Preferably, the duplex regions of the siRNA formed by the ds RNA or by the DNA polypeptide include about 15-30 base pairs, more preferably, about 19-25 base pairs. The siRNA duplex region length may be any positive integer between 15 and 30 nucleotides.

The siRNA of the invention derived from ds RNA may include partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the invention may include a 3' overhang. As used herein, a "3' overhang" refers to at least one unpaired nucleotide extending from the 3'-end of an RNA strand. Thus in an embodiment, the siRNA may includes at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

Both strands of the siRNA molecule may include a 3' overhang, the length of the overhangs can be the same or different for each strand. Preferably, the 3' overhang may be present on both strands of the siRNA, and is 2 nucleotides in length. The 3' overhangs may also be stabilized against degradation. For example, the overhangs may be stabilized by including purine nucleotides, such as adenosine or guanosine nucleotides, by substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

As described above, the RNA duplex portion of the siRNA may be part of a hairpin structure. The hairpin structure may further contain a loop portion positioned between the two sequences that form the duplex. The loop can vary in length. In some embodiments, the loop may be 5, 6, 7, 8, 9, 10, 11, 12 or 13 nucleotides in length. The hairpin structure may also contain 3' or 5' overhang portions. In some embodiments, the overhang is a 3' or a 5' overhang 0, 1, 2, 3, 4 or 5 nucleotides in length.

The siRNA of the invention may be obtained using a number of techniques known to those of skill in the art. For example, the siRNA may be chemically synthesized using appropriately protected ribonucleoside phosphoramidites and a conventional DNA/RNA synthesizer. The siRNA may be synthesized as two separate, complementary RNA molecules, or as a single RNA molecule with two complementary regions. Commercial suppliers of synthetic RNA molecules or synthesis reagents include Dharmacon Research (Lafayette, Colo., USA), Pierce Chemical (Rockford, Ill., USA), Glen Research (Sterling, Va., USA), ChemGenes (Ashland, Mass., USA) and Cruachem (Glasgow, UK).

siRNA Vectors

The siRNA of the present invention may also be expressed from a recombinant plasmid either as two separate, complementary RNA molecules, or as a single RNA molecule with two complementary regions.

Selection of vectors suitable for expressing siRNA of the invention, methods for inserting nucleic acid sequences for expressing the siRNA into the plasmid, and methods of delivering the recombinant plasmid to the cells of interest are within the skill in the art. Methods for constructing recombinant DNA vectors and the production of DNA may be found in Sambrook et al., infra, for example.

The siRNA of the present invention may be a polynucleotide sequence cloned into a plasmid vector and expressed using any suitable promoter. Suitable promoters for expressing siRNA of the invention from a plasmid include, but are not limited to, the H1 and U6 RNA pol III promoter sequences and viral promoters including the viral LTR, adenovirus, SV40, and CMV promoters. Additional promoters known to one of skill in the art may also be used, including tissue specific, inducible or regulatable promoters for expression of the siRNA in a particular tissue or in a particular intracellular environment. The vector may also include additional regulatory or structural elements, including, but not limited to introns, enhancers, and polyadenylation sequences. These elements may be included in the DNA as desired to obtain optimal performance of the siRNA in the cell and may or may not be necessary for the function of the DNA. Optionally, a selectable marker gene or a reporter gene may be included either with the siRNA encoding polynucleotide or as a separate plasmid for delivery to the target cells. Additional elements known to one of skill in the art may also be included.

The siRNA may also be expressed from a polynucleotide sequence cloned into a viral vector that may include the elements described above. Suitable viral vectors for gene delivery to a cell include, but are not limited to, replication-deficient viruses that are capable of directing synthesis of all virion proteins, but are incapable of making infections particles. Exemplary viruses include, but are not limited to lentiviruses, adenoviruses, adeno-associated viruses, retroviruses, and alphaviruses.

Adenovirus, AAV, and lentiviral vectors may be used for gene delivery to the nervous system, including the central nervous system and the peripheral nervous system, where cell division is limited, to infect terminally differentiated cells without the need for cell division. (Davidson et al., *Nat. Genet.* 3:219-223, 1993; Mastrangeli et al., *Clin. Res.* 41:223A (Abstract), 1993; Ghadge et al., *Gene Ther.* 2:132-137, 1995; Xiao et al., *Exp. Neurol.* 144:113-124, 1997; McCown et al., *Brain Res.* 713:99-107, 1996; Davidson and Bohn, *Exp. Neurol.* 144(1):125-30, 1997; Choi-Lundberg, D. L. and Bohn, M. C, *Stem Cell Biology and Gene Therapy*, Quesenberry, P. J., Stein, G. S., Forget, B. and Weissman, S. (Eds), J. Wiley & Sons, New York, pp. 503-553, 1998; Chamberlin et al., *Brain Res.* 793:169-175, 1998; Blomer et al., *J. Virol.* 71:6641-6649, 1997; Zufferey et al., *Nat. Biotechnol.* 15:871-875, 1997; Kordower et al., Exp. Neurol. 160:1-16, 1999). The recombinant lentivirus vectors remain capable of infecting non-dividing cells when deleted of accessory proteins (Johnston et al., *J. Virol.* 73:4991-5000, 1999, Naldini, *Throm. Haemat.* 82:552-554, 1999).

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA or RNA duplex into a host cell include, but are not limited to, calcium phosphate precipitation, lipofection, DEAE-dextran, particle bombardment, microinjection, electroporation, immunoliposomes, lipids, cationic lipids, phospholipids, or liposomes and the like. One skilled in the art will understand that any method may be used to deliver the DNA or RNA duplex into the cell.

One mode of administration to the CNS uses a convection-enhanced delivery (CED) system. This method includes: a) creating a pressure gradient during interstitial infusion into white matter to generate increased flow through the brain interstitium (convection-supplementing simple diffusion); b) maintaining the pressure gradient over a lengthy period of time (24 hours to 48 hours) to allow radial penetration of the migrating compounds (such as: neurotrophic factors, antibodies, growth factors, genetic vectors, enzymes, etc.) into the gray matter; and c) increasing drug concentrations by orders of magnitude over systemic levels. Using a CED system, DNA, RNA duplexes or viruses can be delivered to many cells over large areas of the brain. Any CED device may be appropriate for delivery of DNA, RNA or viruses. In some embodiments, the device is an osmotic pump or an infusion pump. Both osmotic and infusion pumps are commercially available from a variety of suppliers, for example Alzet Corporation, Hamilton Corporation, Alza, Inc., Palo Alto, Calif.).

Biological methods to introduce the nucleotide of interest into a host cell include the use of DNA and RNA viral vectors. For mammalian gene therapy, it is desirable to use an efficient means of inserting a copy gene into the host genome. Viral vectors have become the most widely used method for inserting genes into mammalian, e.g., human cells.

Delivery of the recombinant nucleotides to the host cell may be confirmed by a variety of assays known to one of skill in the art. Assays include Southern and Northern blotting, RT-PCR, PCR, ELISA, and Western blotting, by way of example.

Virus Production

Infective virus particles will be produced from the viral vectors of the present invention using standard methodology, known to one of skill in the art. The methods generally involve introducing the viral vector containing the siRNA encoding polynucleotide into a producer cell. By way of example, the producer cell for a lentiviral vector generally includes gag/pol and env coding sequences. AAV virus production also includes introducing a helper construct into the producer cell, where the helper construct includes coding regions capable of being expressed in the producer cell to complement helper functions missing from the replication deficient viral vector. For AAV vectors helper functions include, but are not limited to, ORFs, namely the rep and cap coding regions, or functional homologues thereof; and helper functions from herpes virus or adenovirus, such as E1A, E2, E3 and E4. The production of virus particles also includes culturing the producer cell to produce virions. The siRNA expression vector, and if necessary, helper construct(s) for AAV can be introduced into the producer cell, either simultaneously or serially, using standard transfection techniques known to one of skill in the art (Zoltukhin et al., *Gene Therapy*, 6:973-985, 1999).

The virions are then harvested from the supernatant of transfected cells, isolated by freeze/thaw cycles and centrifugation. The virions may be purified by binding to a heparin-agarose column, eluted, and concentrated. For in vivo delivery, siRNA virions may be purified by fast performance liquid chromatography (FPLC).

Delivery of Virions to Target Cells

The siRNA virions formed from the siRNA vectors may be delivered to target cells of the central or peripheral nervous system, or both, or any target cell from which the therapeutic protein can have an effect on a nervous system disorder or any target cell affected by a synucleinopathy. Preferably, the siRNA virions are added to the cells at the appropriate multiplicity of infection according to standard transduction methods appropriate for the particular target cells. Titers of siRNA virions to administer can vary, depending upon the target cell type and the particular viral vector, and may be determined by those of skill in the art without undue experimentation. siRNA virions are preferably administered to the cell in a therapeutically-effective amount. siRNA virions may be administered in a physiologically acceptable carrier. In general, a "physiologically acceptable carrier" is one that is not toxic or unduly detrimental to cells. Exemplary physiologically acceptable carriers include sterile, pyrogen-free, phosphate buffered saline. Physiologically-acceptable carriers include pharmaceutically-acceptable carriers.

The siRNA virions may be delivered to a target cell by any method known to one of skill in the art, including, but not limited to injection into the delivery site tissue. By way of example, for delivery to a specific region of the central nervous system, the siRNA virions may be administered by microinjection, infusion, convection enhanced delivery (CED), electroporation or other means suitable to directly deliver the composition directly into the delivery site tissue through a surgical incision. The delivery is generally accomplished slowly, such as at a rate of about 0.2-1 µl per minute. Pursuant to the invention, administration of siRNA virions into selected regions of a subject's brain may be made by drilling a hole and piercing the dura to permit the needle of a microsyringe or micropipette to be inserted. A stereotaxic apparatus may be used to assist in delivering the virions to the specific target cells. Alternatively, siRNA virions may be delivered by lumbar puncture, for example, to the cerebral spinal fluid or delivered intraventricularly. The siRNA virions can be injected intrathecally into a spinal cord region. In another example, virions may be delivered to muscle in order to deliver siRNA to the terminals of motor neurons or sensory neurons. As will be understood by one of skill in the art, virions may be delivered to any cell by any means.

EXAMPLES

The invention will now be illustrated by the following non-limiting examples.

Example 1

Determination of a Target Region of Synuclein

Different regions of the target mRNA appear to be differentially accessible and/or sensitive to siRNA-mediated gene silencing. In order to determine target regions for siRNA-mediated gene silencing, synthetic duplex RNAs directed against different regions of h-α-syn coding sequence may be used to determine the ideal target sequence for RNA interference. Various parameters can be used to determine which sites are the most suitable target sites within the target RNA sequence. These parameters include, but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siRNA molecules for efficacy, for example by using Western blot screens.

siRNAs may be directed against target regions in SEQ ID NO: 1, preferably against target regions in SEQ ID NO: 5, and more preferably against target regions in the following region: GCAGCCACTGGCTTTGTCAAAAGGAC-CAGTTGGGCAAGAATGAAGAAGGAGC-CCCACAGGAA (SEQ ID NO: 6) and AAGGACCAGT-TGGGCAAGAAT (SEQ ID NO: 7). Exemplary regions in the open reading frame of the α-syn gene, against which siRNAs my be directed, identified by the selection criteria listed above include, but are not limited to the following regions listed in Table 1. The regions identified for siRNA-targeted down regulation of synuclein gene expression will be tested using synthetic RNA duplexes transfected into cells and synuclein gene expression will be assayed using Western blotting probed with a synuclein antibody. As described below in Example 9, two siRNA duplexes, SEQ ID NO: 7, listed in Table 1 and SEQ ID NO: 16, a non-responsive region, were made to exemplify how one can determine suitable target sequences.

TABLE 1

| siRNA target sequence | SEQ ID NO: | Target Position in SEQ ID NO: 5 |
| --- | --- | --- |
| AAGGACCAGTTGGGCAAGAAT | 7 | 288 |
| AACAGTGGCTGAGAAGACCAA | 8 | 158 |
| AAAAAGGACCAGTTGGGCAAG | 9 | 285 |
| AAAAGGACCAGTTGGGCAAGA | 10 | 286 |
| AAAGGACCAGTTGGGCAAGAA | 11 | 287 |
| AAGATATGCCTGTGGATCCTG | 12 | 340 |
| AAATGCCTTCTGAGGAAGGGT | 13 | 376 |
| AATGCCTTCTGAGGAAGGGTA | 14 | 377 |
| AAGACTACGAACCTGAAGCCT | 15 | 400 |

Example 2

Generation of a Synuclein siRNA Expression Vector

Synuclein siRNA expression vectors may be generated based on the results of the RNA duplex transfection studies discussed above. Alternatively, synuclein siRNA expression vectors may be generated based on the selection criteria discussed above without first testing the target with a siRNA duplex. Nucleotide sequences complementary to the RNA duplexes or identified synuclein targets may be cloned into a plasmid vector containing a promoter operatively linked to the nucleotide sequence. The nucleotide may further include a hairpin and a loop. The construct may be generated using molecular biology techniques known to one of skill in the art. A synuclein siRNA expression vector was made based on the siRNA duplex region identified as a target for down regulation of synuclein to exemplify how one can construction expression vectors targeting synuclein gene expression and is described below in Example 10.

Example 3

Lentiviral Vector-Based siRNA

Lentiviral constructs including a RNA polymerase III promoter-driven siRNA for down regulating α-synuclein were generated. By way of example, the region of the α-syn gene identified in SEQ ID NO: 7 was included in the lentiviral construct. The lentiviral construct was constructed by digesting the pBCSK/H1 α-Syn si expression vector described in detail below in Example 13. The pBCSK/H1 α-Syn si expression vector was digested with NotI and EcoRV. The NotI-EcoRV fragment was ligated into a lentiviral backbone construct, plentilox3.7 that has been digested with Xba1 and Xho1, blunted by filling in with Klenow and digested with NotI. This dual cassette vector LV-α-Syn-shRNA-CMV-EGFP co-expresses enhanced green fluorescent protein (EGFP) as a reporter gene, and hα-Syn-targeting shRNA under the control of CMV and human H1 promotors, respectively. The plentilox3.7 vector is described in Rubinson D A, et al., *Nat. Genet.* 33(3):401-6, 2003.

A lentiviral shuttle plasmid harboring wild type hα-Syn (LV-CMV-hα-Syn) was cloned using a pcDNA3.1 plasmid containing wild type h-α-syn obtained from Yong-Jian Liu (University of Pittsburgh, Pittsburgh, Pa.). h-α-syn was cut out of the plasmid with KpnI and XbaI digests and ligated into psP72. This intermediate plasmid was digested with BglII and the fragment ligated into the lentiviral backbone, HR'CMVGFPWSIN (Didier Trono, Swiss Institute of Technology, Lausanne, Switzerland) previously digested with BamHI and XhoI to remove GFP. Expression of h-α-syn was confirmed by transfecting the LV-CMV-h-α-Syn shuttle plasmid into 293T cells and staining for immunoreactivity to h-α-syn.

Example 4

AAV Vector-Based siRNA

AAV constructs including a RNA polymerase III promoter-driven siRNA for down regulating α-synuclein were generated. By way of example, the region of the α-syn gene identified in SEQ ID NO: 7 was included in an AAV2 construct. A dual cassette AAV-α-syn-shRNA CMV-hrGFP vector was constructed to co-express a α-syn short hairpin RNA under the control of the human Pol III (H1) promotor and the marker gene hrGFP under the control of the CMV promoter. The AAV construct was constructed by digesting the pBCSK/H1 α-Syn si expression vector described in detail below in Example 10. Using the pBCSK/H1 α-Syn si expression vector as a template, an H1 α-syn-shRNA expression cassette was PCR amplified using primers with 5' MLu1 and 3' Ase1 restriction sites and ligated into MLu1 and Ase1 sites of an AAV-hrGFP plasmid (Stratagene). The resulting vector includes 5' and 3' inverted terminal repeats of AAV2 flanking H1 driven α-syn-shRNA and CMV driven hrGFP with globin IVS inserted between CMV and hrGFP using hGH poly A. The following primers were used to amplify the H1 α-syn-shRNA expression cassette:

(SEQ ID NO: 37)
5'-ATACGCGTAAGCTTGATATCGAATTCGAACGCTGAC-3'

(SEQ ID NO: 38)
5'-TTACTATTAATAACTAGCTCCTGGCGGCCGCTCTAGTTT
CCAAAAAG-3'

Example 5

Virus Production from Lentiviral-Based siRNA

Self-inactivating lentiviral vectors were packaged as previously described with minor modifications (Zufferey, *Curr. Top. Microbiol. Immunol.*, 261: 107-121, 2002; Karolewski et al., *Hum. Gene Ther.* 14: 1287-1296, 2003.) Briefly, 293T cells were transfected with a four-plasmid vector system i.e., the lentiviral/H1siRNA construct described in Example 3, a packaging plasmid pHRCMVδ8.92, pRSVrev and the VSV-G envelope plasmid, pMDG (Follenzi, A and Naldini, L., *Methods Mol. Med.* 69, 259-274, 2002). Two days post-transfection, the supernatant was collected and ultra centrifuged at 141,000×g for 1.5 h. The pellet was resuspended in media (DMEM supplemented with 10% FBS or PBS). The vector was purified by FPLC or by passing through a 0.45 µm filter and frozen at −80° C. The viral titer was determined by infecting 293T cells with serial dilutions, and also by real time PCR as previously described in Lizee G, et al., *Hum. Gene Ther.* 10; 14(6):497-507, 2003. The RNAi activity of each recombinant lentivirus batch was be tested in HeLa cells as described below.

Example 6

Virus Production from AAV Vector-Based siRNA

The components needed for the production of recombinant AAV-2 particles in the helper virus-free system include a shuttle plasmid containing the gene of interest and AAV-2 ITRs, a packaging plasmid known to one of skill in the art for clinical applications, and 293 cells. Recombinant AAV (rAAV) vectors, for example, the AAV vector described in Example 4, was packaged and purified as described previously with minor modifications (Zoltukhin et al., *Gene Therapy*, 6:973-985, 1999). In brief, 293 cells were plated at $2 \times 10^6$ cells per 100-mm tissue culture plate in 10 ml DMEM containing 10% FBS and antibiotics 48 h prior to transfection. Shuttle and packaging plasmids were used at a ratio of 1:3 for $CaCl_2$ transfection. At 2-4 h before transfection, fresh, pre-warmed medium was added to the 293 cells and then the DNA/$CaCl_2$/HPES suspension was added dropwise, swirling gently to distribute the DNA suspension evenly. After 48 h, the medium was replaced with 10 ml of fresh DMEM growth medium and plates were incubated for another 24 h. After 72 h incubation, the cells were harvested into 50-ml falcon tubes and 15 ml lysis buffer (50 mM Tris-HCl (pH 8.5) and 150 mM sodium chloride) was added to 20 plates worth of cells.

The cell suspension was subjected to three rounds of freeze/thawing by alternating tubes between a dry ice-ethanol bath and a 37° C. water bath, vortexing briefly after each thaw. Following centrifugation at 3 000 g for 5 min at room temperature, the supernatant was transferred to a fresh tube and octylglucopyranoside (to 0.5%) and benzonase (36 units/ml) was added and the solution incubated for 45 min at 37° C. After centrifuging at 3 000 g for 5 min, the supernatant was collected.

The viral particles were purified by a two-step FPLC procedure using a POROS-PI anion exchange column followed by a heparin column. The supernatant was loaded onto a POROS-PI (Applied Biosciences) FPLC column in 20 mM MES, 20 mM HEPES, 20 mM NaOAc, 0.15 M KCl, pH 6.7 and eluted in 20 mM MES, 20 mM HEPES, 20 mM NaOAc, 0.35 M KCl, pH 6.7 at 10 mL/minute (Kaludov, N., *Hum. Gene Ther.*, 13(10) 1235-43, 2002). The eluate as detected at 280 nm will be concentrated with an Amicon Centriplus 100 000 MWCO filter and resuspended in 20 mM Tris, 150 mM NaCl, pH 8.0. The vector was further purified by loading onto a Heparin Hi-Trap FPLC column (Pharmacia) in 20 mM Tris, 150 mM NaCl, pH 8.0, and eluting with a 7 minute gradient from 150 mM NaCl to 1 M NaCl at 4 mL/minute (Clark et al., *Hum. Gene Ther.*, 10: 1031-1039, 1999). The eluate as detected at 280 nm was concentrated with an Amicon Centriplus 100 000 MWCO filter and resuspended in PBS, 5% sorbitol, 0.001% PF68 (BASF) for storage at −80° C. Electron microscopy of uranyl acetate stained vector stocks was used to assess the ratio of packaged to empty particles. The biological titer was assessed according to the single stranded DNA copy number using quantitative real-time PCR. The rAAV vector capsid particle number was determined using an ELISA kit (Progen Biotechnik GMBH, Heidelberg, Germany) based on the A20 capsid protein and checked for in vitro expression of the siRNA using 293 cells. Samples were tested for bacterial contamination using a limulus amebocyte lysate kinetic-QCL kit (Bio Whittaker) according to the manufacturer's protocol.

For the in vivo studies, rAAV siRNA vectors of the preferred embodiment were purified as described above.

Example 7 siRNA Inhibition of Cell Death and Increased Sensitivity to Cell Death Induced by MPTP and MG132

Overexpression of wild-type or A53T or A30P mutated h-α-syn in human dopaminergic cell lines is known to trigger cell death, and also increases sensitivity to cell death induced by proteasome inhibitor MG132 (Petrucelli et al., 2002, *Neuron*, 36 (6):1007-19). Furthermore, α-syn null mice exhibit striking resistance to MPTP-induced degeneration of dopamine (DA) neurons, which suggests that genetic and environmental factors that lead to Parkinson's disease may interact with a common molecular pathway (Dauer et al, 2002, *Proc. Natl. Acad. Sci, U.S.A.*, 99, 14524-14529). siRNA-mediated silencing of wild-type and mutant h-α-syn will be investigated to determine whether the siRNA protects against α-syn overexpression-associated cell death, and results in increased resistance against the toxic effects of MPTP and MG132.

HeLa cells and the human dopaminergic cell line SH-SY5Y (obtained from American Type Culture Collection, ATCC, Manassas, Va.) were used to investigate siRNA mediated down regulation of α-synuclein (wild-type and mutant), cell death and toxicity. HeLa cells were grown in Dulbecco's Modified Eagle's Medium (DMEM) supplemented with 10% FBS (Gibco, Carlsbad, Calif.) and 1% antibiotics (10,000 IU/ml penicillin base and 10,000 ug/ml streptomycin base, Gibco) at 37° C. with 5% $CO_2$. SH-SY5Y cells were grown in DMEM: F12 (1:1) medium supplemented with 10% FBS at 37° C. with 5% $CO_2$.

Lentiviral constructs described above in Example 3 were used as well as mutant constructs generated in the plentilox3.7 vector. SH-SY5Y cells will be infected with human α-synuclein expressing lentiviruses in the presence or absence of lentiviral RNA-H1 promoter-driven α-syn siRNA expression system. At 48-60 h post-infection, cell viability of the cells will be examined using MTT assay (Petrucelli et al., *Neuron*, 36 (6):1007-19, 2002), and annexinV (Molecular Probes, Eugene, Oreg.) and Hoechst staining procedures (Oberhammer F, et al., *J. Cell Sci.*, 104 317-26, 1993) as are known to one of skill in the art.

Parallel cultures will be treated with MPP+ (10-50 µM, for 48 h) or with MG132 (5-10 µM) for 24 h, after which MTT assay, and annexinV and Hoechst staining analysis will determine cell viability. Western blot and real time PCR analyses of parallel cultures will determine the expression of h-α-syn under different treatment conditions.

Example 8

In Vivo Delivery of siRNA in Rats

Targeted overexpression of wild-type or mutant h-α-syn in the rat nigrostriatal system results in progressive neurodegenerative pathology in the nigrostriatal DA neurons, and provides a rat model of Parkinson's disease that reproduces some of the cardinal pathological, neurochemical, and behavioral features of the human disease (Kirik et al, 2002, *J. Neurosci.,* 222(7): 2780-91). This rat model of Parkinson's disease is characterized by death of nigral DA neurons, dystrophic neuritis, and α-synuclein-positive cytoplasmic axonal inclusions and will be used to examine siRNA down regulation using a lentiviral or AAV vector expressing a region of the α-syn gene.

Stereotaxic injections and immunocytochemistry were carried out as previously described with minor modifications. (Connor et al., *Gene Ther.,* 6:1936-1951, 1999.) Adult Wistar rats (225-250 g; Harlan, Indianapolis, Ind.) maintained according to CMRC animal house and NIH guidelines and maintained on 12 hr light/dark cycle with ad libitum access to food and water, were used for in vivo experiments. Briefly, under anesthesia, 3 μl of the hα-syn lentivirus LV-CMV-h-α-syn (titer=6×$10^7$ TU/ml) and 3 μl the lentivirus LV α-syn-shRNA-CMV-EGFP (titer=6.5×$10^9$ TU/ml) was stereotaxically injected into the left substantia nigra (SN) using a 10 μl Hamilton syringe with a 30-guage needle at a rate of 0.5 μl/min. The coordinates for the striatal injections were 1.2 mm rostral, 2.6 mm lateral and 5.0 mm ventral from the bregma. The right SN served as a control which was co-injected with the ha-syn lentivirus and a control EGFP lentivirus lacking the ha-syn shRNA. At two weeks post injection, anesthetized rats were perfused transcardially with 0.9% saline followed by 4% paraformaldehde in PBS. The brains were removed, cute in half sagitally and post-fixed in 4% paraformaldehyde for 24 hrs, and then cyroprotected in 30% sucrose. Frozen coronal section (40 μm) were made through the striatum using a sliding microtome (Leica, McHenry, Ill.). For immunofluorescence, sections were incubated overnight at 4° C. with the h-α-syn antibody LB509 (1:100 dilution) or the anti-neuronal nuclei antibody, NeuN (Chemicon Inc., Temecula, Calif. 1:200 dilution). Following washing, the sections were treated with goat anti-mouse IgG conjugated to cyanine 3 (Cy3™; 1:500 dilution, Jackson ImmunoResearch, West Grove, Pa.). Immunofluorescence was examined by confocal fluorescence microscopy.

Striatal sections analyzed by immunofluorescence and confocal microscopy, revealed EGFP and ha-syn co-labeled cells in control striatae. Co-labeled cells were absent in striatae injected with the h-α-syn shRNA virus, showing total in vivo silencing of ha-syn in striatal neurons. Similar experiments were conducted using AAV h-α-syn shRNA CMVrhGFP virus generated from the vector described in Example 4 and sections from the substantia nigra were analyzed by immunofluorescence and confocal microscopy. Results showed greater than 90% in vivo silencing of hα-syn in nigral neurons using the AAV virus.

In other experiments, overexpression-induced neurodegeneration of nigrostriatal system is generally apparent in 6-8 weeks. Rats treated as described above, will be sacrificed for immunohistochemical analysis 8 weeks after the first injection. Immunohistochemical stainings will be performed on free-floating brain sections using antibodies raised against tyrosine hydroxylase (Chemicon, Temecula, Calif.) and wild-type or mutant h-α-syn. The number of TH+ neurons in the SN and striatum, and α-syn-immunoreactive cell bodies along with neurodegenerative cell bodies in the SN pars compacta will be determined for each treatment group. The expression of siRNA targeting α-syn or its mutants will be confirmed by in situ hybridization of the brain sections using appropriate digoxigenin-labelled riboprobes known to one of skill in the art.

At 24 weeks post-injection, the rats will be subjected to behavioral testing, including "amphetamine rotation" and "paw placement" tests to assess motor impairments. In animals with a unilateral lesion of the nigrostriatal dopaminergic (DA) system, the injection of drugs that act to release dopamine, such as amphetamine, will induce rotational behavior towards the denervated striatum. Animals will turn away from the hemisphere where there is greater amphetamine-stimulated dopamine release and greater dopamine receptor stimulation.

Amphetamine-induced rotational activity will be recorded for 60 min following an i.p. injection of 5 mg DL-amphetamine per kg body weight. Rats will be placed in a plastic bowl (depth 18 cm; diameter 38 cm) and video taped and rated. Base line amphetamine rotation tests will be performed 7 days before the 6-OHDA lesions and the results will be used to assign the side of the subsequent 6-OHDA lesion. Rats exhibiting net clockwise turns will be lesioned in the left stiatum, while rats exhibiting net counter-clockwise turns will be lesioned in the right striatum. Following the 6-OHDA lesion, amphetamine-induced rotational behavior will be tested 14 and 35 days after lesioning.

The number of clockwise and counter-clockwise turns will be counted and expressed as the number of net rotations per minute to the lesioned (ipsilateral) hemisphere (net rotations per minute to ipsilateral hemisphere=ipsilateral rotations–contralateral rotations/time). Repeated-factor, two-way ANOVA will be performed to evaluate the rotational behavior. Rotational behavior will be evaluated pre-lesioning with 6-OHDA, and post lesioning, and with and without administration of the siRNA lentiviral or AAV vector. A decrease in the ipsilateral rotational behavior when compared with control groups will indicate a therapeutic effect of the administration of the siRNA lentiviral or AAV vector.

Spontaneous exploratory forelimb use will be scored using forelimb asymmetry analysis. The number of ipsilateral, contralateral and both paw placements performed against the chamber wall during vertical/lateral explorations and the paw used to land following exploration will be quantified during slow-motion playback of the videotaped session. The results will be presented as percent of total ipsilateral forelimb use by first calculating the percentage of ipsilateral wall (ipsilateral wall placement/ipsilateral wall+contralateral wall+both wall placement×100) and ipsilateral land (ipsilateral land placement/ipsilateral land+contralateral land+both land placement×100) movements. The percentage of ipsilateral wall and ipsilateral land placements will then be added together and divided by two. The calculation will assure that the wall and land movements will be weighted evenly and will result in a measure of ipsilateral forelimb use relative to total forelimb movement. Rats that exhibit less than five forelimb placements during the 5 minutes will be removed from analysis. One-way ANOVA will be used to analyze the preferential use of the ipsilateral forelimb post 6-OHDA lesioning compared with control groups. A decrease in the preferential use of the ipsilateral forelimb when compared with control groups will indicate a therapeutic effect of the administration of the siRNA.

Example 9

In Vivo Delivery of siRNA in a Mouse Model of Parkinson's Disease-Short-Term Studies A transgenic model of Parkinson's Disease involving α-synuclein will be used to determine the effects of selectively interfering with human α-synuclein expression in midbrain DA neurons, as well as to determine the effects of RNA interference by shRNA vector administration.

In some experiments, an α-synuclein transgenic mouse generated using the full-length 9.2 kb rat TH promoter to target wild type or a double mutant (A30P and A53T) h-α-syn expression to catecholamine neurons will be used. (Richfield, et al., 2002, *Exp. Neurol.*, 175(1): 35-38.) These mice display an increased density of dopamine transporter (DAT) and increased sensitivity to MPTP. The double mutant mice show increased sensitivity to amphetamine and age-related declines in motor coordination. Locomotor activity in response to apomorphine is also increased in these mice. Levels of striatal DA, DOPAC and HVA are significantly decreased only in the double mutant mice. (Id., Thiruchelvam, et al. 2004, *Eur. J. Neurosci.*, 19(4): 845-54.)

Two lines of mice will be studied: h2α-syn-5 which is heterozygous for wild type h-α-syn and line hm$^2$α-syn-39 which is heterozygous for a doubly-mutated h-α-syn (A30P and A53T). (Id.) Mouse lines will be maintained by standard techniques using normal C57Bl6 females from Jackson Labs as breeders. Transgenic mice will be screened by PCR of tail genomic DNA by amplifying a 469 bp fragment of the coding sequence using forward and reverse primers, hSYNU1, caggtaccgacagttgtggtgtaaaggaat (SEQ ID NO. 35 and hSYNL1, gatagctataaggcttcaggttcgtagtct (SEQ ID NO. 36), respectively. In these mice, expression of h-α-syn is high in catecholamine neurons in the SN, VTA and LC and respective terminal regions.

To investigate silencing of h-α-syn, heterozygous male mice (2 mos.) will receive a 2 μl injection of either h2α-syn-5 or hm$^2$α-syn-39 in one side of the brain and a 2 μl injection of control vector into the other SN. One month after viral injection, expression of h-α-syn will be studied by immunohistochemistry, western blotting for α-synuclein protein, and real-time PCR for α-synuclein mRNA.

Immunohistochemistry will be performed on mice one month after viral injection. Mice will be euthanized by cardiac perfusion with 4% paraformaldehyde following a prewash with buffered saline and the brain tissue will be prepared for histology. Forty micron frozen sections will be collected using RNase free reagents. Some sections will be stained for immunofluorescence (IF) to α-syn using a mouse monoclonal human specific antibody (Affiniti Research, Plymouth Meeting, Pa.) and a goat-anti-mouse secondary IgG conjugated to Cy3 (near red fluorescence; excitation, 557 nm; emission, 615 nm). Sections will be co-stained for TH-IF using a polyclonal rabbit antibody (Chemicon) and a secondary IgG conjugated to Cy5 (far red fluorescence; excitation, 650 nm; emission, 670 nm). Confocal microscopy using a Zeiss 10 Meta Confocal Microscope (Laser Scanning Microscope) (LSM) will be used to capture images of DA neurons that are infected with the AAV viruses by co-localization of hGFP fluorescence. For the purposes of this analysis, it will be assumed that GFP fluorescent neurons also express the shRNA against α-syn. Levels of α-syn IF will be quantified in a minimum of 100 GFP positive and 100 negative DA neurons in the substantia nigra at matched anatomical levels of both sides of the brain. Data will be analyzed by two-way ANOVA and the significance of inter-group differences determined by applying the Students' two-tailed t-test. Sections of striatum will also be studied using analogous approaches to determine whether levels of hu α-synuclein in DA fibers in terminal regions have been affected.

For molecular analyses of the effects of the shRNA vector against expression of h-α-syn, mice will be lightly anesthetized with pentobarbital and euthanized by decapitation one month after vector injections. Brains will be rapidly removed and the striata and ventral nesencephalons dissected, frozen in dry ice and stored at −80° C. Protein and RNA will be isolated from these regions on both sides of the brains using Trizol reagent as previously reported. (Kozlowski, et al., 2000, *Society for Neuroscience Abstracts*, 26: 1794.) Levels of human and mouse α-syn protein will be analyzed by western blotting and 2-D gel electrophoresis. Levels of human and mouse α-syn mRNAs will be determined by RT-PCR using previously published methods (Id.) and primer and probes specific to human or mouse α-syn. Primers and probes will be designed using the Primer Express Program (Applied Biosciences, Inc., Salt Lake City, Utah).

Example 10

In Vivo Delivery of siRNA in a Mouse Model of Parkinson's Disease-Long-Term Studies Chronic effects of silencing hu α-synuclein on DA neurons will be examined using transgenic models of Parkinson's Disease as described above in Example 9. shRNA α-synAAV vectors (described above) will be used to chronically depress expression of hu α-synuclein in nigral DA neurons in h2α-syn-5 and hm$^2$α-syn-39 mice. Mice will be evaluated for effects on DA neurons using histological, neurochemical and behavioral endpoints.

Experimental or control AAV vector will be injected bilaterally into the nigra of 2 month old male mice (2 μl/side). Groups of mice will be euthanized at 10 months and 20 months and evaluated for the effects on DA neurons using the following endpoints:

Locomotor Activity: Mice will be assessed for horizontal, vertical and ambulatory activity in chambers equipped with an infrared photobeam using an Opto-Varimex Minor instrument (Columbus Instruments International, Columbus, Ohio) (described in Thiruchelvam, et al. 2004, *Eur. J. Neurosci.*, 19(4): 845-54.) Mice will be familiarized with the testing chambers by placing them in these chambers for 45 minutes one week prior to the onset of testing. Testing will commence when mice are 2 months of age prior to vector injections and will continue every 2 months until mice are 10 or 20 months of age with the final testing done several days prior to euthanasia. Photobeam breaks will be recorded each minute for 45 minutes with activity counts totaled in 3 minute blocks across the session. Overall effects of treatment, age and transgene status will be analyzed with repeated-measures ANOVA followed by individual ANOVAs and Bonferroni-Dunn tests to compare treatments. (Id.)

Locomotor activity after apomorphine challenge: h2α-syn-5 and hm$^2$α-syn-39 mice treated with shRNA α-syn or control vector will be injected with saline or apomorphine (1.5 mg/kg, i.p.) on subsequent trials at 2 weeks prior to euthanasia and tested for locomotor activity. Testing and data analysis will be as described above.

Amphetamine c-fos induction in striatal neurons. Induction of c-fos immunoreactivity in nuclei of striatal target neurons of DA fibers has been used as a measure of degree of integrity and function of the DA terminals. (Connor et al., 1999, *Gene Therapy*, 6: 1936-1951; Kozlowski et al., 2000, Exp. Neurol., 166: 1-15; Robertson et al, 1989, Brain Research, 503: 346-349.) Mice will be injected with D-amphetamine (5 mg/kg, i.p.) 2 hours prior to euthanasia and sections of striatum stained for c-fos-IR. (Kozlowski et al., 2000, Exp. Neurol., 166: 1-15.) The number of c-fos-IR nuclei will be counted at 2 anatomical levels of striatum using NeuroLucida software (Microbrightfield Laboratories, Williston, Vt.). Data will be analyzed by ANOVA and Students' t-test.

Neuroprotection of DA Neurons: At 10 or 20 months of age, mice will be euthanized by cardiac perfusion with 4% paraformaldehyde and 40 μm sections of nigra and striatum prepared as described above. Sections will be stained for TH-IR using a mouse monoclonal antibody to TH (Chemicon International, Temecula, Calif.) using diaminobenzidine using DAB method (brown stain) and co-stained for IR to GFP using nickel enhanced diaminobenzidine using DAB (black stain) and a polyclonal antibody against hrGFP. (Id.) The numbers of TH-IR neurons with and without GFP staining indicating infection with the AAV virus will be determined through the entire substantia nigra using an optional fractionator and StereoInvestigator™ software (Microbrightfield Laboratories, Williston, Vt.). (Id.) Sections will also be evaluated using IF for GFP, h-α-syn-IR and TH-IR as described above to verify decreased expression of h-α-syn in DA neurons.

Density of DA fibers in striatum: Sections of striatum will be stained for TH-IF or the dopamine transporter (DAT)-IF or the vesicular monoamine transporter (VMAT)-IF using polyclonal antibodies and co-stained for h-α-syn-IF using a monoclonal antibody specific to human as described above. Using confocal microscopy to capture images at two anatomical level through the striatum, the density of each marker on each side of the brain will be assessed using Openlab 4.0.3 software (Improvision, Inc., Lexington, Mass.).

Detection of proteinase K resistant α-syn positive fibers in striatum: To study wither increased high MW species of α-syn are more abundant in the transgenic mouse lines, as well as to determine if interfering with expression of h-α-syn will reduce the levels of any high MW species, sections of striatum will be stained for TH-IR using DAB. Sections will then be digested with proteinase K and stained for h-α-syn using nickel enhanced DAB. (Neumann, et al., 2002, *J. Clin. Invest.*, 110: 1429-39.)

Example 11 siRNA Duplex Down Regulation of α-Syn Gene Expression

As described above in Example 1, regions of the α-syn gene were identified for siRNA duplex formation. Two regions were selected for targeting with siRNAs. A first target sequence in the α-syn DNA in SEQ ID NO: 1 is:

```
AATGTTGGAGGAGCAGTGGTG        (SEQ ID NO: 16)
```

Thus, a siRNA duplex, Synthetic siRNA Duplex A, of the present invention, complementary to SEQ ID NO: 16, targeting this sequence, and which has 3' dTdT overhangs on each strand (overhangs shown in bold), is:

```
Sense:
5'-UGUUGGAGGAGCAGUGGUGdTdT-3'    (SEQ ID NO: 17)

Antisense:
3'-dTdTACAACCUCCUCGUCACCAC-5'    (SEQ ID NO: 18)
```

A second target sequence in the α-syn DNA in SEQ ID NO: 1 is:

```
AAGGACCAGTTGGGCAAGAAT        (SEQ ID NO: 7)
```

A siRNA duplex, Synthetic siRNA Duplex B, of the present invention, complementary to SEQ ID NO: 7, targeting this sequence, and which has 3' dTdT overhangs on each strand (overhangs shown in bold), is:

```
Sense:
5'-GGACCAGUUGGGCAAGAAUdTdT-3'    (SEQ ID NO: 19)

Antisense:
3'-dTdTCCUGGUCAACCCGUUCUUA-5'    (SEQ ID NO: 20)
```

Each synthetic siRNA oligo duplex, described as A and B above, was heated to 90° C. for 2 min followed by incubation at 37° C. for 60 min and frozen until use.

To demonstrate silencing of the α-syn gene, synthetic siRNA duplexes A and B were used to transfect HeLa cells (American Type Culture Collection). HeLa cells were cultured in DMEM (Gibco) supplemented with 10% fetal bovine serum. These cells were grown in 6-well plates and transfected with wild-type h-α-syn expression plasmid in the presence or absence of synthetic siRNA duplexes A and B (100 nM) using LipofectAMINE2000® (Invitrogen, Carlsbad, Calif.) according to the manufacture's instructions. At 48 or 72 hours post-transfection, the cells were harvested for preparation of whole cell lysates. Lysates were run on SDS-PAGE and electrophoretically transferred to nitrocellulose membranes for Western blotting. Western blotting was performed, using standard techniques known to one of skill in the art. Briefly, blocked membranes were incubated overnight at 4° C. with a h-α-syn-specific monoclonal antibody LB509 (Zymed, South San Francisco, Calif., 1:50 dilution) or a polyclonal α-syn antibody from BD Biosciences (Mountain View, Calif., 1:500 dilution). Following 1 hr incubation at room temperature with a horseradish peroxidase-coupled secondary antibody (1:250 dilution), the blots were washed and immunodetection was carried out using ECL detection reagents (Amersham Biosciences, Buckinghamshire, UK). The blots were then stripped and re-probed using either a β-actin antibody (Santa Cruz Biotechnology, Santa Cruz, Calif., 1:1000 dilution) or a monoclonal antibody against α-tubulin (Sigma, St. Louis, Mo., 1:100000) and detected as described above to confirm equal loading in all the lanes.

The results of Western blotting show that at both 48 and 72 hours, siRNA duplex B down regulated expression of α-syn while siRNA A showed little or no effect on α-syn expression as compared to control levels of α-syn expression. Reprobing of the blot with actin confirmed equal loading of lysates in all lanes.

Example 12

In Vivo Delivery of Synthetic siRNA Duplexes

The synthetic siRNA duplexes A and B described above in Example 11 will be used for in vivo delivery to mice to demonstrate the down regulation of α-syn expression. The mice used for in vivo delivery studies will include wild type mice and transgenic mice (describe above in Example 9) including h2α-syn-5 mice which are heterozygous for wild type h-α-syn and hm²α-syn-39 mice which are heterozygous for a doubly-mutated h-α-syn (A30P and A53T).

The synthetic siRNA duplexes A and B will be formed as described above with a 19-bp oligoribonucleotide region and dinucleotide overhangs on the 3' end of each strand and including either 2'-O-(2-methoxyethyl)-modified nucleotide residues linked by means of a phosphorothioate group or deoxynucleotide residues linked by means of a phosphodiester group. (See Thakker et al, 2004, *PNAS,* 101(49):17270-17275.) The oligonucleotides described above (SEQ ID NOS: 17 and 18 for duplex A and SEQ ID NOS: 19 and 20 for duplex B) will be annealed in an isotonic RNAi buffer (100 mM potassium acetate/30 mM Hepes-KOH/2 mM magnesium acetate/26 mM NaCl, pH 7.4) at 37° C. Osmotic minipumps will be filled with the isotonic RNAi buffer alone or buffer with either siRNA duplex A or siRNA duplex B (0.01-0.4 mg per day) for infusion at a rate of 12 or 6 µl/day for 1 week (Alzet model 1007D, Durect, Cupertino, Calif.) or 2 weeks (Alzet model 1002), respectively.

A brain-infusion cannula (Plastics One, Roanoke, Va.) will be stereotaxically placed, as described by the manufacturer, for infusion from the s.c. implanted minipump into the dorsal third ventricle (anteriorposterior, −0.5 mm; mediolateral, 0 mm; dorsoventral, −3 mm relative to bregma). Appropriate anesthesia will be delivered to the mice.

Following administration of the synthetic siRNA duplexes A and B, mice will be assessed as described above in Examples 9 and 10. In addition, mice will be assessed for locomotor activity on days −1 and 0 prior to implanting the cannula and on day 3, 6, 9, 12 and 14 post implantation.

Example 13 siRNA Expression Vector Construct Targeting α-Syn

A siRNA expression vector was constructed based on the down regulation of α-syn gene expression obtained in cells transfected with siRNA duplex B. PCR-based cloning was used to clone H-1 RNA polymerase III promoter from human genomic DNA. The H1 promoter was amplified from human genomic DNA using the following oligos:

```
                                          (SEQ ID NO: 31)
5'-CCATGGAATTCGAACGCTGACGTCATCAACCCGCTC-3'
and (SEQ ID NO: 32)
5'-CGGATCCAGATCTGTGGTCTCATACAGAACTTATAAGATTC
CC-3'.
```

The PCR-amplified product was digested with EcoR1 and BamH1, and ligated to EcoR1 and BamH1 digested pBc-SK+ vector (Strategene, La Jolla, Calif.) to create a pBC/H-1 construct.

Forward and reverse hairpin oligonucleotides were generated for targeting the region of the α-syn gene identified by the siRNA duplex B in Example 9 above having the following sequences (the hairpin loop is identified in bold):

```
                                          (SEQ ID NO: 21)
5'-GATCCCCGGACCAGTTGGGCAAGAATTCAAGAGAATTCTT

GCCCAACTGGTCCTTTTTGGAAA-3'

(SEQ ID NO: 22)
5'-CTAGTTTCCAAAAAGGACCAGTTGGGCAAGAATTCTCTTGA

AATTCTTGCCCAACTGGTCCGGG-3'
```

The oligonucleotides (1.6 uM each in 0.1M NaCl) were annealed by heating at 80° C. for 2 min followed by incubation at 35° C. for 2 hours. The annealed oligonucleotides were then inserted into the BglII and Xba1 sites of the pBCSK-H1 construct to form the pBCSK-H1α-synuclein shRNA expression vector. Sequencing using techniques known to one of skill in the art was used to confirm the sequence accuracy of the construct. (See Sanger et al., *Proc. Natl. Acad. Sci. U.S.A.,* 74, 5463-5467.)

HeLa cells were transfected with a human α-synuclein expression vector (gift of Dr. Stefanis, Stefanis et al., *J. Neurosci.,* 21(24):9549-60, 2001) in the presence or absence of the siRNA expression vector, pBC/H1 α-Syn siRNA, containing the annealed hairpin oligos of SEQ ID NOS: 21 and 22 driven by the H-1 pol III promoter. The α-syn expression vector was co-transfected with the pBC/H1 α-Syn siRNA expression vector in the ratio of 1:3 (Vec. Syn si3) or 1:1 (Vec. Syn si1). At 48 h post-transfection, the cells were harvested and Western blot analysis was performed as described above.

Western blotting using a synuclein antibody shows down regulation of α-syn expression by the pBCSK/H1 α-Syn shsiRNA expression vector, in both ratios 1:3 and 1:1, as compared to control expression with the α-syn expression vector alone. Equal loading of lysates was confirmed by reprobing the membrane with an actin antibody (described above).

Example 14

Delivery of siRNA Virions to SH-SY5Y Cells

Studies were performed in cultured SH-SY5Y cells, a human dopaminergic neuroblastoma cell line that expresses human α-synuclein. Lentiviruses, proven to be highly effective method for transferring foreign genes into non-dividing and terminally differentiated cells such as the neuronal cells, were used to deliver an α-syn shsiRNA construct (described in Example 10) to the SH-SY5Y cells at a multiplicity of infection (MOI) of 10. At 72 hours post-infection, cells were harvested and whole cell lysates were prepared for Western blotting. α-syn antibody (BD Transduction Laboratories, BD Biosciences, Oak Park, Ill.) was used to probe the membrane following a standard blotting protocol. The blot was then stripped and reprobed using a monoclonal anti-α-tubulin antibody (Sigma, St. Louis, Mo.) to confirm equal loading of the lysates.

Western blotting results showed that endogenous α-syn expression was down regulated by the lentiviral siRNA construct as compared to the control lentiviral vector alone.

Example 15

Allele Specific siRNA Targeting of Mutant α-Syn

A variety of synthetic 21 nucleotide siRNAs were made to determine a target for down regulation of the expression of the A53T mutant α-syn allele. Regions surrounding the A53T site in the mutant α-syn were used to generate synthetic siRNA duplexes, as described above in Example 1. The mutant adenosine residue corresponding to the guanine to adenosine mutation at nucleotide 203 of SEQ ID NO: 1 is included in the target region and the position of the mutant residue in the target siRNA is indicated by the name of the siRNA. For example, the nucleotide sequence of si 9, referring to the sense strand, is a 21 nucleotide sequence with the adenosine residue corresponding to the mutation at position 9 of the sense strand, si 10 and si 11 correspond to the adenosine residue at positions 10 and 11 respectively of the sense strand. si 9, 10 refers to the sense strand wherein the adenosine residue corresponding to the 203 mutation is at position 9 and an artificial mutation of cytosine to guanine at position 10 of the siRNA. si 9,12 refers to the sense strand wherein the adenosine residue corresponding to the 203 mutation is at position 9 and an artificial mutation of adenine to thymidine is at position 12 of the siRNA. The RNA sense strand for each of the synthetic nucleotides is listed below in Table 2 with the mutated residues in bold.

TABLE 2 siRNA targeting A53T mutant human α-synuclein

| Mutant | Synthetic RNA sense strand | DNA |
|---|---|---|
| si 9 | AUGGUGUGACAACAGUGGCUG (SEQ ID NO: 23) | ATGGTGTGACAACAGTGGCTG (SEQ ID NO: 24) |
| Si 10 | CAUGGUGUGACAACAGUGGCU (SEQ ID NO: 25) | CATGGTGTGACAACAGTGGCT (SEQ ID NO: 26) |
| si 9, 12 | AUGGUGUGACAUCAGUGGCUG (SEQ ID NO: 27) | ATGGTGTGACATCAGTGGCTG (SEQ ID NO: 28) |
| Si 11 | GCAUGGUGUGACAACAGUGGC (SEQ ID NO: 29) | GCATGGTGTGACAACAGTGGC (SEQ ID NO: 30) |
| Si 9, 10 | AUGGUGUGAGAACAGUGGCUG (SEQ ID NO: 33) | ATGGTGTGAGAACAGTGGCTG (SEQ ID NO: 34) |

As described above, the synthetic siRNA duplexes may include additional residues, such as, but not limited to, 3' overhangs. The regions identified for down regulating the expression of A53T mutant h-α-syn may also be used, for example, in synthetic oligonucleotides, including hairpin duplexes, and in vector constructs as described for the wild-type α-syn described above.

The synthetic RNA oligonucleotides listed in Table 2 were used to generate synthetic siRNA duplexes for cell transfection assays similar to Example 9. HeLa cells were co-transfected with EGFP and wild type h-α-syn expression plasmids or EGFP and human A53T mutant expression plasmids, as described above in Example 12, in the presence or absence of synthetic siRNA duplex si 9, si 10, si 11, si 9, 10 or si 9,12 (10 nM). At 48 h post-transfection, the cells were harvested for Western blot analysis. The membrane was probed with a h-α-syn-specific monoclonal antibody (Zymed Laboratories, South San Francisco, Calif.) and then stripped and reprobed with actin (described above) to confirm equal loading in all the lanes. Results of Western blotting showed siRNA duplex si 9 allele specifically down-regulated A53T mutant α-syn expression and not wild type human α-syn expression.

A similar strategy will be used to determine siRNA duplexes for down regulating expression of A30P mutant α-syn. The targeted regions identified using synthetic siRNA duplexes may also be used to generate plasmid and viral constructs to down regulate expression of wild-type, A53T, and A30P mutant α-syn.

Example 16

Dose Dependent Down Regulation of α-Syn Using Synthetic Duplex B

Dose response and specificity of the siRNA-mediated down regulation of α-syn was shown. An EGFP or a h-α-syn expression plasmid was co-transfected into HeLa cells with varying concentrations of Synthetic siRNA Duplex B (described above in Example 9) or a non-specific synthetic siRNA directed against the firefly luciferase gene. Synthetic siRNA Duplex B concentrations for the co-transfection were 0.1 nM, 1 nM, 5 nM, 10 nM, 25 nM, 50 nM, and 100 nM. At 72 hrs post-transfection, the cells were harvested for Western blot analysis. Western blotting was performed as described above.

Results of the Western blotting showed dose-dependent silencing of h-α-syn expression in lanes with all concentrations of Synthetic siRNA Duplex B and no effect of the non-specific siRNA in the controls.

Example 17

Dose Dependent Down Regulation of α-Syn Using α-Syn shRNA Plasmid

Dose response and specificity of the siRNA-mediated down regulation of α-syn by the shRNA plasmid described in Example 10 was shown. An EGFP expression plasmid (0.5 μg) and a h-α-syn expression plasmid (2.0 μg) were co-transfected into HeLa cells with varying concentrations of pBCSK-H1-α-syn-shRNA expression plasmid (0.01 μg, 0.2 μg, 1.0 μg, 4.0 μg or 5 μg) (described above in Example 10) or 5.0 μg pBCSK-H1 plasmid control. At 48 hrs post-transfection, the cells were harvested for Western blot analysis. Western blotting was performed as described above.

Results of the Western blotting showed dose-dependent silencing of h-α-syn expression with the α-syn shRNA expression plasmid and no effect on expression of EGFP.

Example 18

Liposomal Complex Preparation for In Vivo siRNA Delivery siRNA vectors and synthetic siRNA duplexes may be delivered to cells using liposomes. Any method know to one skilled in the art may be used for forming liposomes. Exemplary methods are given below.

Liposomes will be prepared by lipid-film hydration using HEPES-buffered saline (pH 6.5) as the hydration buffer. The liposomes will be hydrated in 6 successive cycles of freezing (−80° C.) and thawing (60° C.). Unilamellar liposomes will be formed by extrusion using a 10-ml capacity thermostatted extruder (Northern Lipids, Vancouver, BC, Canada). Extrusion will be performed through polycarbonate membranes by using the appropriate pore size and the number of extrusions required to reach the desired liposome size (approximately 65 nm), which will be determined by light scattering (Beckman Coulter, Fullerton, Calif.). Cholesterol will be obtained from Calbiochem (San Diego, Calif.). 1,2-dioleoyl-sn-glycero-3-phosphocholine (DOPC) and 1,2-distearoyl-sn-glycero-3-phosphoethanolamine-N-[methoxy(polyethylene glycol)-2000] (PEG-DSPE will be purchased from Avanti Polar Lipids (Alabaster, Ala.). Liposomes will be composed of a 3:2 (mol:mol) phospholipid/cholesterol mixture. Liposome concentrations for infusion studies will be 2 mM phospholipid.

Liposomes may also be prepared using 1,2 Dioleoyl-3-trimethylammonium-propane (DOTAP) (Roche Diagnostics). (Sioud et al., 2003, *Bioch. Biophys. Res. Comm.*, 312: 1220-1225.) siRNAs for inclusion in the complexes will be annealed in transfection buffer (20 mM HEPES, 150 mM NaCl, pH 7.4) at 3 ug/ml.

For i.v. injection of mice, liposomal complexes will be prepared as follows. 20-100 µg of siRNAs in transfection buffer will be transferred into a sterile eppendorf tube. In a separate sterile polystyrene tube, 50 µg of DOTAP will be mixed with 120 µl transfection buffer and then the siRNA mixture will be transferred to the polystyrene tube containing the DOTAP and then incubated at room temperature for 30 min (the mixture may be cloudy, but no precipitates or aggregates should be visible). About 200 µl of the mixture will be injected via the tail vein, using a 1-ml syringe and 27-guage needle. Charge ratio of DOTAP and siRNA will vary from 1:2 to 2:1. After the desired amount of time, the mice will be sacrificed and analyzed as discussed above.

For i.p. injection of mice, 50-100 µg of siRNAs in 60 µl of transfection buffer will be pipetted into a sterile eppendorf tube. In a separate sterile polystyrene tube, 100-200 µg of DOTAP will be mixed with 300-600 µl transfection buffer and then both solutions mixed gently by pipetting several times. After incubation at room temperature for 30 min., the mixture will be adjusted to 1 ml with transfection buffer, prior to i.p. injection using a 2 ml syringe and 27-guage needle. Charge ratio of DOTAP to siRNAs will vary form 1:1 to 4:1. After the desired amount of time, the mice will be sacrificed and analyzed as discussed above.

Example 19

In Vivo Delivery Using CED

CED may be used to deliver α-syn DNA, vectors, viruses, and synthetic siRNA duplexes to the brain. By way of example, CED may be performed on rats as described below.

Rats will be anesthetized with Isoflurane (Baxter, Deerfield, Ill.) by inhalation (3 L mixed with oxygen) and will be placed in a small-animal stereotaxic frame (David Kopf Instruments; Tujunga, Calif.). A sagital skin incision will be made and burr holes will be placed in the skull by a twist drill, 0.5 mm anterior to the bregma and 3 mm to the right and left of the midline. CED will be used to infuse solutions containing the α-syn DNA, vectors, viruses, or synthetic siRNA duplexes and controls into each hemisphere. To minimize trauma and reflux flow, customized needle cannula will be created by inserting silica capillary tubing (100 µm in diameter, Polymicro Technologies; Phoenix, Ariz.) into a 24-guage needle fused with a Teflon® tube (0.02") and connected to a programmable microinfusion pump (Bioanalytical Systems, West Lafayette, Ind.). The loading chamber (Teflon® tubing, 1/16" OD×0.03" ID) and attached infusion chamber (1/16" OD×0.02" ID) will be filled with a total volume of 60 µl of each mixture per loading line. Two cannulae (one per hemisphere) will be placed in the rat striatum, 5 mm below the dura. The infusion rate will be 0.2 µl/min for 10 min and 0.5 µl/min for 6 min.

Samples will be analyzed according to the short and long term experiments described above.

Although the invention herein has been described in connection with an embodiment thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. A method of reducing expression of a synuclein gene in a cell, said method comprising introducing into a cell a siRNA in an amount effective to down regulate expression of said synuclein gene,
wherein said siRNA comprises a nucleotide sequence has at least 90% complementarity to SEQ ID NO: 7, SEQ ID NO: 9, SEQ ID NO: 10, or SEQ ID NO: 11 and has a length of 21-30 nucleotides.

2. The method of claim 1 wherein said nucleotide sequence is complementary to 15 to 21 consecutive nucleotides of SEQ ID NO: 7.

3. The method of claim 1 wherein said siRNA is introduced into said cell in a vector encoding said siRNA.

4. The method of claim 1 wherein said siRNA forms a hairpin structure comprising a loop.

5. A method of reducing expression of a synuclein gene in a cell, said method comprising: introducing a vector encoding a siRNA into a cell, the siRNA being introduced in an amount effective to down regulate expression of said synuclein gene, wherein said siRNA is encoded by a nucleotide sequence at least 90% identical to SEQ ID NO:21.

6. The method of claim 1 wherein said cell is a central nervous system cell or a peripheral nervous system cell.

7. A method of treating a neurodegenerative disease or a synucleinopathy in a subject comprising administering to said subject a therapeutically effective amount of a siRNA comprising a nucleotide sequence having at least 90% identity to SEQ ID NO: 7, SEQ ID NO: 9, SEQ ID NO: 10, or SEQ ID NO: 11 and having a length of 21-30 nucleotides, wherein the expression of a synuclein gene is down regulated.

8. The method of claim 3, wherein the vector is an expression vector comprising a promoter operably linked to the siRNA.

9. The method of claim 3, wherein the vector is a viral vector.

10. The method of claim 8, wherein the promoter is a constitutive promoter or a regulatable promoter operatively linked to the nucleotide sequence encoding the siRNA.

11. The method of claim 1, wherein the siRNA comprises a 3' overhang of at least one unpaired nucleotide.

12. The method of claim 1, wherein the siRNA comprises a 5' overhang of at least one unpaired nucleotide.

13. The method of claim 3, wherein the vector is selected from the group consisting of adenoviral, lentiviral, poliovirus, adeno-associated viral, HSV, and murine Maloney-based viral vector.

14. The method of claim 3, wherein the vector comprises a Pol III H-1 promoter operatively linked to said siRNA.

15. The method of claim 7, wherein the neurodegenerative disease is Parkinson's disease.

16. The method of claim 7, wherein said siRNA forms a hairpin structure comprising a loop.

17. The method of claim 7, wherein an expression vector encodes the siRNA.

* * * * *

UNITED STATES PATENT AND TRADEMARK OFFICE
CERTIFICATE OF CORRECTION

| | | |
|---|---|---|
| PATENT NO. | : 8,389,487 B2 | Page 1 of 1 |
| APPLICATION NO. | : 12/693101 | |
| DATED | : March 5, 2013 | |
| INVENTOR(S) | : Martha C. Bohn et al. | |

It is certified that error appears in the above-identified patent and that said Letters Patent is hereby corrected as shown below:

On the Title Page

Left column, item (73) replace "Ann & Robert Lurie" with --Ann & Robert H. Lurie--.

Signed and Sealed this
Tenth Day of December, 2013

Margaret A. Focarino
*Commissioner for Patents of the United States Patent and Trademark Office*

SEQUENCE LISTING

<160> NUMBER OF SEQ ID NOS: 38

<210> SEQ ID NO 1
<211> LENGTH: 1543
<212> TYPE: DNA
<213> ORGANISM: Homo sapiens

<400> SEQUENCE: 1

```
ggagtggcca ttcgacgaca gtgtggtgta aaggaattca ttagccatgg atgtattcat      60
gaaaggactt tcaaaggcca aggagggagt tgtggctgct gctgagaaaa ccaaacaggg     120
tgtggcagaa gcagcaggaa agacaaaaga gggtgttctc tatgtaggct ccaaaaccaa     180
ggagggagtg gtgcatggtg tggcaacagt ggctgagaag accaaagagc aagtgacaaa     240
tgttggagga gcagtggtga cgggtgtgac agcagtagcc cagaagacag tggagggagc     300
agggagcatt gcagcagcca ctggctttgt caaaaaggac cagttgggca agaatgaaga     360
aggagcccca caggaaggaa ttctggaaga tatgcctgtg gatcctgaca atgaggctta     420
tgaaatgcct tctgaggaag ggtatcaaga ctacgaacct gaagcctaag aaatatcttt     480
gctcccagtt tcttgagatc tgctgacaga tgttccatcc tgtacaagtg ctcagttcca     540
atgtgcccag tcatgacatt tctcaaagtt tttacagtgt atctcgaagt cttccatcag     600
cagtgattga agtatctgta cctgccccca ctcagcattt cggtgcttcc ctttcactga     660
agtgaataca tggtagcagg gtctttgtgt gctgtggatt ttgtggcttc aatctacgat     720
gttaaaacaa attaaaaaca cctaagtgac taccacttat ttctaaatcc tcactatttt     780
```

-continued

```
tttgttgctg ttgttcagaa gttgttagtg atttgctatc atatattata agatttttag    840 gtgtcttta atgatactgt ctaagaataa tgacgtattg tgaaatttgt taatatatat    900
aatacttaaa aatatgtgag catgaaacta tgcacctata aatactaaat atgaaatttt    960
accattttgc gatgtgtttt attcacttgt gtttgtatat aaatggtgag aattaaaata  1020
aaacgttatc tcattgcaaa aatatttat ttttatccca tctcacttta ataataaaaa   1080
tcatgcttat aagcaacatg aattaagaac tgacacaaag gacaaaaata taagttatt    1140 aatagccatt tgaagaagga ggaatttag aagaggtaga gaaatggaa cattaaccct     1200 acactcggaa ttccctgaag caacactgcc agaagtgtgt tttggtatgc actggttcct  1260
taagtggctg tgattaatta ttgaaagtgg ggtgttgaag acccaacta ctattgtaga    1320 gtggtctatt tctcccttca atcctgtcaa tgtttgcttt atgtattttg gggaactgtt   1380
gtttgatgtg tatgtgttta taattgttat acattttaa ttgagcctt tattaacata    1440 tattgttatt tttgtctcga aataatttt tagttaaaat ctatttgtc tgatattggt    1500 gtgaatgctg taccttctg acaataaata atattcgacc atg                     1543
```

<210> SEQ ID NO 2
<211> LENGTH: 140
<212> TYPE: PRT
<213> ORGANISM: Homo sapiens

<400> SEQUENCE: 2

```
Met Asp Val Phe Met Lys Gly Leu Ser Lys Ala Lys Glu Gly Val Val
1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 3
<211> LENGTH: 1543
<212> TYPE: DNA
<213> ORGANISM: Homo sapiens

<400> SEQUENCE: 3

```
ggagtggcca ttcgacgaca gtgtggtgta aaggaattca ttagccatgg atgtattcat     60
gaaaggactt tcaaaggcca aggagggagt tgtggctgct gctgagaaaa ccaaacaggg   120
tgtggcagaa gcaccaggaa agacaaaaga gggtgttctc tatgtaggct ccaaaaccaa   180
ggagggagtg gtgcatggtg tggcaacagt ggctgagaag accaaagagc aagtgacaaa   240
tgttggagga gcagtggtga cgggtgtgac agcagtagcc cagaagacag tggagggagc   300
agggagcatt gcagcagcca ctggctttgt caaaaaggac cagttgggca agaatgaaga   360
```

```
aggagcccca caggaaggaa ttctggaaga tatgcctgtg gatcctgaca atgaggctta    420
tgaaatgcct tctgaggaag ggtatcaaga ctacgaacct gaagcctaag aaatatcttt    480
gctcccagtt tcttgagatc tgctgacaga tgttccatcc tgtacaagtg ctcagttcca    540
atgtgcccag tcatgacatt tctcaaagtt tttacagtgt atctcgaagt cttccatcag    600
cagtgattga agtatctgta cctgccccca ctcagcattt cggtgcttcc ctttcactga    660
agtgaataca tggtagcagg gtctttgtgt gctgtggatt ttgtggcttc aatctacgat    720
gttaaaacaa attaaaaaca cctaagtgac taccacttat ttctaaatcc tcactatttt    780
tttgttgctg ttgttcagaa gttgttagtg atttgctatc atatattata agattttag     840 gtgtcttta atgatactgt ctaagaataa tgacgtattg tgaaatttgt taatatatat     900
aatacttaaa aatatgtgag catgaaacta tgcacctata aatactaaat atgaaatttt     960
accattttgc gatgtgtttt attcacttgt gtttgtatat aaatggtgag aattaaaata    1020
aaacgttatc tcattgcaaa atatttttat ttttatccca tctcacttta ataataaaaa    1080
tcatgcttat aagcaacatg aattaagaac tgacacaaag gacaaaaata taagttatt    1140 aatagccatt tgaagaagga ggaattttag aagaggtaga gaaatggaa cattaaccct     1200 acactcggaa ttccctgaag caacactgcc agaagtgtgt tttggtatgc actggttcct    1260
taagtggctg tgattaatta ttgaaagtgg ggtgttgaag accccaacta ctattgtaga    1320
gtggtctatt tctcccttca atcctgtcaa tgtttgcttt atgtattttg gggaactgtt    1380
gtttgatgtg tatgtgttta taattgttat acattttaa ttgagccttt tattaacata    1440
tattgttatt tttgtctcga aataatttt tagttaaaat ctattttgtc tgatattggt    1500
gtgaatgctg tacctttctg acaataaata atattcgacc atg                     1543
```

<210> SEQ ID NO 4
<211> LENGTH: 1543
<212> TYPE: DNA
<213> ORGANISM: Homo sapiens

<400> SEQUENCE: 4

```
ggagtggcca ttcgacgaca gtgtggtgta aaggaattca ttagccatgg atgtattcat     60
gaaaggactt tcaaaggcca aggagggagt tgtggctgct gctgagaaaa ccaaacaggg    120
tgtggcagaa gcagcaggaa agacaaaaga gggtgttctc tatgtaggct ccaaaaccaa    180
ggagggagtg gtgcatggtg tgacaacagt ggctgagaag accaaagagc aagtgacaaa    240
tgttggagga gcagtggtga cgggtgtgac agcagtagcc cagaagacag tggagggagc    300
agggagcatt gcagcagcca ctggctttgt caaaaaggac cagttgggca agaatgaaga    360
aggagcccca caggaaggaa ttctggaaga tatgcctgtg gatcctgaca atgaggctta    420
tgaaatgcct tctgaggaag ggtatcaaga ctacgaacct gaagcctaag aaatatcttt    480
gctcccagtt tcttgagatc tgctgacaga tgttccatcc tgtacaagtg ctcagttcca    540
atgtgcccag tcatgacatt tctcaaagtt tttacagtgt atctcgaagt cttccatcag    600
cagtgattga agtatctgta cctgccccca ctcagcattt cggtgcttcc ctttcactga    660
agtgaataca tggtagcagg gtctttgtgt gctgtggatt ttgtggcttc aatctacgat    720
gttaaaacaa attaaaaaca cctaagtgac taccacttat ttctaaatcc tcactatttt    780
tttgttgctg ttgttcagaa gttgttagtg atttgctatc atatattata agattttag     840 gtgtcttta atgatactgt ctaagaataa tgacgtattg tgaaatttgt taatatatat     900
aatacttaaa aatatgtgag catgaaacta tgcacctata aatactaaat atgaaatttt     960
```

```
accatttttgc gatgtgtttt attcacttgt gtttgtatat aaatggtgag aattaaaata    1020
aaacgttatc tcattgcaaa aatatttttat tttttatccca tctcacttta ataataaaaa    1080
tcatgcttat aagcaacatg aattaagaac tgacacaaag gacaaaaata taaagttatt    1140
aatagccatt tgaagaagga ggaattttag aagaggtaga gaaaatggaa cattaaccct    1200
acactcggaa ttccctgaag caacactgcc agaagtgtgt tttggtatgc actggttcct    1260
taagtggctg tgattaatta ttgaaagtgg ggtgttgaag acccccaacta ctattgtaga    1320 gtggtctatt tctcccttca atcctgtcaa tgtttgcttt atgtattttg gggaactgtt    1380
gtttgatgtg tatgtgttta taattgttat acattttttaa ttgagccttt tattaacata    1440
tattgttatt tttgtctcga aataattttt tagttaaaat ctattttgtc tgatattggt    1500
gtgaatgctg tacctttctg acaataaata atattcgacc atg                       1543
```

```
<210> SEQ ID NO 5
<211> LENGTH: 423
<212> TYPE: DNA
<213> ORGANISM: Homo sapiens

<400> SEQUENCE: 5
atggatgtat tcatgaaagg actttcaaag gccaaggagg gagttgtggc tgctgctgag     60
aaaaccaaac agggtgtggc agaagcagca ggaaagacaa agagggtgt tctctatgta    120 ggctccaaaa ccaaggaggg agtggtgcat ggtgtggcaa cagtggctga aagaccaaa    180 gagcaagtga caaatgttgg aggagcagtg gtgacgggtg tgacagcagt agcccagaag    240
acagtggagg gagcagggag cattgcagca gccactggct ttgtcaaaaa ggaccagttg    300
ggcaagaatg aagaaggagc cccacaggaa ggaattctgg aagatatgcc tgtggatcct    360
gacaatgagg cttatgaaat gccttctgag gaagggtatc aagactacga acctgaagcc    420
taa                                                                   423
```

```
<210> SEQ ID NO 6
<211> LENGTH: 63
<212> TYPE: DNA
<213> ORGANISM: Homo sapiens

<400> SEQUENCE: 6
gcagccactg gctttgtcaa aaaggaccag ttgggcaaga atgaagaagg agccccacag     60
gaa                                                                    63
```

```
<210> SEQ ID NO 7
<211> LENGTH: 21
<212> TYPE: DNA
<213> ORGANISM: Homo sapiens

<400> SEQUENCE: 7
aaggaccagt tgggcaagaa t                                                21
```

```
<210> SEQ ID NO 8
<211> LENGTH: 21
<212> TYPE: DNA
<213> ORGANISM: Homo sapiens

<400> SEQUENCE: 8
aacagtggct gagaagacca a                                                21
```

-continued

```
<210> SEQ ID NO 9
<211> LENGTH: 21
<212> TYPE: DNA
<213> ORGANISM: Homo sapiens

<400> SEQUENCE: 9
aaaaaggacc agttgggcaa g                                              21

<210> SEQ ID NO 10
<211> LENGTH: 21
<212> TYPE: DNA
<213> ORGANISM: Homo sapiens

<400> SEQUENCE: 10
aaaaggacca gttgggcaag a                                              21

<210> SEQ ID NO 11
<211> LENGTH: 21
<212> TYPE: DNA
<213> ORGANISM: Homo sapiens

<400> SEQUENCE: 11
aaaggaccag ttgggcaaga a                                              21

<210> SEQ ID NO 12
<211> LENGTH: 21
<212> TYPE: DNA
<213> ORGANISM: Homo sapiens

<400> SEQUENCE: 12
aagatatgcc tgtggatcct g                                              21

<210> SEQ ID NO 13
<211> LENGTH: 21
<212> TYPE: DNA
<213> ORGANISM: Homo sapiens

<400> SEQUENCE: 13
aaatgccttc tgaggaaggg t                                              21

<210> SEQ ID NO 14
<211> LENGTH: 21
<212> TYPE: DNA
<213> ORGANISM: Homo sapiens

<400> SEQUENCE: 14
aatgccttct gaggaaggt a                                               21

<210> SEQ ID NO 15
<211> LENGTH: 21
<212> TYPE: DNA
<213> ORGANISM: Homo sapiens

<400> SEQUENCE: 15
aagactacga acctgaagcc t                                              21

<210> SEQ ID NO 16
<211> LENGTH: 21
<212> TYPE: DNA
<213> ORGANISM: Homo sapiens

<400> SEQUENCE: 16
aatgttggag gagcagtggt g                                              21
```

```
<210> SEQ ID NO 17
<211> LENGTH: 21
<212> TYPE: DNA
<213> ORGANISM: Artificial Sequence
<220> FEATURE:
<223> OTHER INFORMATION: Sense RNA targeting SEQ ID NO: 16
<220> FEATURE:
<221> NAME/KEY: misc_feature
<222> LOCATION: (20)..(21)
<220> FEATURE:
<221> NAME/KEY: misc_feature
<222> LOCATION: (20)..(21)
<223> OTHER INFORMATION: T is deoxythymidine

<400> SEQUENCE: 17
uguuggagga gcaguggugt t                                              21

<210> SEQ ID NO 18
<211> LENGTH: 21
<212> TYPE: DNA
<213> ORGANISM: Artificial Sequence
<220> FEATURE:
<223> OTHER INFORMATION: Antisense synthetic RNA targeting SEQ ID NO: 17
<220> FEATURE:
<221> NAME/KEY: misc_feature
<222> LOCATION: (20)..(21)
<220> FEATURE:
<221> NAME/KEY: misc_feature
<222> LOCATION: (20)..(21)
<223> OTHER INFORMATION: T is deoxythymidine

<400> SEQUENCE: 18
caccacugcu ccuccaacat t                                              21

<210> SEQ ID NO 19
<211> LENGTH: 21
<212> TYPE: DNA
<213> ORGANISM: Artificial Sequence
<220> FEATURE:
<223> OTHER INFORMATION: Sense artificial RNA targeting SEQ ID NO: 7
<220> FEATURE:
<221> NAME/KEY: misc_feature
<222> LOCATION: (20)..(21)
<223> OTHER INFORMATION: T is deoxythymidine

<400> SEQUENCE: 19
ggaccaguug ggcaagaaut t                                              21

<210> SEQ ID NO 20
<211> LENGTH: 21
<212> TYPE: DNA
<213> ORGANISM: Artificial Sequence
<220> FEATURE:
<223> OTHER INFORMATION: Antisense artificial RNA targeting SEQ ID NO: 7
<220> FEATURE:
<221> NAME/KEY: misc_feature
<222> LOCATION: (20)..(21)
<223> OTHER INFORMATION: T is deoxythymidine

<400> SEQUENCE: 20
auucuugccc aacuggucct t                                              21

<210> SEQ ID NO 21
<211> LENGTH: 64
<212> TYPE: DNA
<213> ORGANISM: Artificial Sequence
<220> FEATURE:
<223> OTHER INFORMATION: oligonucleotide sequence for targeting
      SEQ ID NO: 1
```

```
<400> SEQUENCE: 21
gatccccgga ccagttgggc aagaatttca agagaattct tgcccaactg gtccttttg      60 gaaa                                                                  64

<210> SEQ ID NO 22
<211> LENGTH: 64
<212> TYPE: DNA
<213> ORGANISM: Artificial Sequence
<220> FEATURE:
<223> OTHER INFORMATION: Oligonucleotide sequence for targeting
      SEQ ID NO: 1

<400> SEQUENCE: 22 ctagttttcca aaaaggacca gttgggcaag aattctcttg aaattcttgc ccaactggtc    60
cggg                                                                  64

<210> SEQ ID NO 23
<211> LENGTH: 21
<212> TYPE: RNA
<213> ORGANISM: Artificial Sequence
<220> FEATURE:
<223> OTHER INFORMATION: Sense strand for targeting SEQ ID NO: 24

<400> SEQUENCE: 23
auggugugac aacaguggcu g                                               21

<210> SEQ ID NO 24
<211> LENGTH: 21
<212> TYPE: DNA
<213> ORGANISM: Homo sapiens

<400> SEQUENCE: 24
atggtgtgac aacagtggct g                                               21

<210> SEQ ID NO 25
<211> LENGTH: 21
<212> TYPE: RNA
<213> ORGANISM: Artificial Sequence
<220> FEATURE:
<223> OTHER INFORMATION: Sense strand for targeting SEQ ID NO: 25

<400> SEQUENCE: 25
caugguguga caacaguggc u                                               21

<210> SEQ ID NO 26
<211> LENGTH: 21
<212> TYPE: DNA
<213> ORGANISM: Homo sapiens

<400> SEQUENCE: 26
catggtgtga caacagtggc t                                               21

<210> SEQ ID NO 27
<211> LENGTH: 21
<212> TYPE: RNA
<213> ORGANISM: Artificial Sequence
<220> FEATURE:
<223> OTHER INFORMATION: Sense strand targeting SEQ ID NO: 28

<400> SEQUENCE: 27
auggugugac aucaguggcu g                                               21
```

```
<210> SEQ ID NO 28
<211> LENGTH: 21
<212> TYPE: DNA
<213> ORGANISM: Homo sapiens

<400> SEQUENCE: 28
atggtgtgac atcagtggct g                                              21

<210> SEQ ID NO 29
<211> LENGTH: 21
<212> TYPE: RNA
<213> ORGANISM: Artificial Sequence
<220> FEATURE:
<223> OTHER INFORMATION: Sense strand targeting SEQ ID NO: 30

<400> SEQUENCE: 29
gcauggugug acaacagugg c                                              21

<210> SEQ ID NO 30
<211> LENGTH: 21
<212> TYPE: DNA
<213> ORGANISM: Homo sapiens

<400> SEQUENCE: 30
gcatggtgtg acaacagtgg c                                              21

<210> SEQ ID NO 31
<211> LENGTH: 36
<212> TYPE: DNA
<213> ORGANISM: Artificial Sequence
<220> FEATURE:
<223> OTHER INFORMATION: Sense oligonucleotide for H-1 RNA polymerase
      III promoter

<400> SEQUENCE: 31
ccatggaatt cgaacgctga cgtcatcaac ccgctc                              36

<210> SEQ ID NO 32
<211> LENGTH: 43
<212> TYPE: DNA
<213> ORGANISM: Artificial Sequence
<220> FEATURE:
<223> OTHER INFORMATION: Antisense oligonucleotide for H-1 RNA
      polymerase III promoter

<400> SEQUENCE: 32
cggatccaga tctgtggtct catacagaac ttataagatt ccc                      43

<210> SEQ ID NO 33
<211> LENGTH: 21
<212> TYPE: RNA
<213> ORGANISM: Artificial
<220> FEATURE:
<223> OTHER INFORMATION: si 9, 10

<400> SEQUENCE: 33
auggugugag aacaguggcu g                                              21

<210> SEQ ID NO 34
<211> LENGTH: 21
<212> TYPE: DNA
<213> ORGANISM: Artificial Sequence
<220> FEATURE:
<223> OTHER INFORMATION: si 9, 10

<400> SEQUENCE: 34
atggtgtgag aacagtggct g                                              21
```

```
<210> SEQ ID NO 35
<211> LENGTH: 30
<212> TYPE: DNA
<213> ORGANISM: Artificial sequence
<220> FEATURE:
<223> OTHER INFORMATION: forward oligo for h synuclein

<400> SEQUENCE: 35
caggtaccga cagttgtggt gtaaaggaat                                    30

<210> SEQ ID NO 36
<211> LENGTH: 30
<212> TYPE: DNA
<213> ORGANISM: Artificial Sequence
<220> FEATURE:
<223> OTHER INFORMATION: reverse oligo for h synuclein

<400> SEQUENCE: 36
gatagctata aggcttcagg ttcgtagtct                                    30

<210> SEQ ID NO 37
<211> LENGTH: 36
<212> TYPE: DNA
<213> ORGANISM: Artificial
<220> FEATURE:
<223> OTHER INFORMATION: Forward primer

<400> SEQUENCE: 37
atacgcgtaa gcttgatatc gaattcgaac gctgac                             36

<210> SEQ ID NO 38
<211> LENGTH: 47
<212> TYPE: DNA
<213> ORGANISM: Artificial Sequence
<220> FEATURE:
<223> OTHER INFORMATION: Reverse oligo

<400> SEQUENCE: 38
ttactattaa taactagctc ctggcggccg ctctagtttc caaaaag                 47
```